(12) United States Patent
Lavigne et al.

(10) Patent No.: US 10,385,326 B2
(45) Date of Patent: Aug. 20, 2019

(54) VARIANTS OF GH FAMILY 11 XYLANASE AND POLYNUCLEOTIDES ENCODING SAME

(71) Applicant: NOVOZYMES A/S, Bagsvaerd (DK)

(72) Inventors: James Lavigne, Wake Forest, NC (US); Brian R. Scott, West Sacramento, CA (US); Daniel Sebastian Kolczynski, Nepean (CA)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/314,822

(22) PCT Filed: May 22, 2015

(86) PCT No.: PCT/US2015/032092
§ 371 (c)(1),
(2) Date: Nov. 29, 2016

(87) PCT Pub. No.: WO2015/183710
PCT Pub. Date: Dec. 3, 2015

(65) Prior Publication Data
US 2017/0101635 A1   Apr. 13, 2017

Related U.S. Application Data

(60) Provisional application No. 62/005,200, filed on May 30, 2014.

(51) Int. Cl.
| | | |
|---|---|---|
| *C12N 9/24* | (2006.01) | |
| *C12N 1/21* | (2006.01) | |
| *C12P 19/14* | (2006.01) | |
| *C12P 19/02* | (2006.01) | |

(52) U.S. Cl.
CPC ............ *C12N 9/2482* (2013.01); *C12P 19/02* (2013.01); *C12P 19/14* (2013.01); *C12Y 302/01008* (2013.01)

(58) Field of Classification Search
None
See application file for complete search history.

(56) References Cited

U.S. PATENT DOCUMENTS

| | | | |
|---|---|---|---|
| 5,759,840 A | 6/1998 | Sung | |
| 7,060,482 B1 | 6/2006 | Sung | |
| 7,314,743 B2 | 1/2008 | Clarkson | |
| 7,510,860 B1 | 3/2009 | Sung | |
| 7,695,947 B2 | 4/2010 | Sung | |
| 8,951,751 B2 * | 2/2015 | Sibbesen | ........ C12Y 302/01008 435/18 |
| 2009/0111155 A1 * | 4/2009 | White | .................... A21D 8/042 435/171 |
| 2014/0322764 A1 | 10/2014 | Yanai | |

FOREIGN PATENT DOCUMENTS

| | | | | |
|---|---|---|---|---|
| WO | 2006/012904 A1 | 2/2006 | | |
| WO | 2007/115391 A1 | 10/2007 | | |
| WO | WO-2013077432 A1 * | 5/2013 | ............. | C12N 9/248 |

OTHER PUBLICATIONS

Dumon et al, 2008, J Biol Chem 283, 22557-22564.
Wang et al, 2008,Biotechnol Lett 30(5), 937-944.
WO 2006-012904 A1—Geneseq Access No. AEF76437.
WO 2013-077432 A1—Geneseq Access No. BAP10806.
WO 2013-077432 A1—Geneseq Access No. BAP10809.
WO 2014-020141 A1—Geneseq Access No. BBC27775.

\* cited by examiner

*Primary Examiner* — Robert B Mondesi
*Assistant Examiner* — Todd M Epstein
(74) *Attorney, Agent, or Firm* — Joshua Price

(57) ABSTRACT

The present invention relates to GH Family 11 xylanase variants. The present invention also relates to polynucleotides encoding the variants; nucleic acid constructs, vectors, and host cells comprising the polynucleotides; and methods of using the variants.

15 Claims, 10 Drawing Sheets

Specification includes a Sequence Listing.

US 10,385,326 B2

VARIANTS OF GH FAMILY 11 XYLANASE AND POLYNUCLEOTIDES ENCODING SAME

CROSS-REFERENCE TO RELATED APPLICATIONS

This application is a 35 U.S.C. 371 national application of PCT/US2015/032092 filed May 22, 2015, which claims priority or the benefit under 35 U.S.C. 119 of U.S. provisional application No. 62/005,200 filed May 30, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to variants of GH Family 11 xylanases, polynucleotides encoding the variants, methods of producing the variants, and methods of using the variants.

Description of the Related Art

Xylan, a major component of plant hemicellulose, is a polymer of D-xylose linked by beta-1,4-xylosidic bonds. Xylan can be degraded to xylose and xylo-oligomers by acid or enzymatic hydrolysis. Enzymatic hydrolysis of xylan produces free sugars without the by-products formed with acid (e.g., furans).

Xylanases can be used in various applications such as enzymatic breakdown of agricultural wastes for production of alcoholic fuels, enzymatic treatment of animal feeds to release free sugars, enzymatic treatment for dissolving pulp in the preparation of cellulose, and enzymatic treatment in biobleaching of pulp. In particular, xylanase is useful in the paper and pulp industry to enhance the brightness of bleached pulp, improve the quality of pulp, decrease the amount of chlorine used in the chemical pulp bleaching steps, and to increase the freeness of pulp in recycled paper processes.

Dumon et al., 2008, *Journal of Biological Chemistry* 283: 22557-22564, describe the engineering of hyperthermostability into a GH11 xylanase. Wang and Tao, 2008, *Biotechnology Letters* 30: 937-944, disclose the enhancement of the activity and alkaline pH stability of *Thermobifida fusca* xylanase A by directed evolution.

U.S. Pat. Nos. 5,759,840, 7,510,860, and 7,695,947 disclose modifications of Family 11 xylanases to improve thermophilicity, alkalophilicity and thermostability. U.S. Pat. No. 7,060,482 discloses modified xylanases comprising either a basic amino acid at position 162 corresponding to the *Trichoderma reesei* xylanase (TrX) amino acid sequence, or its equivalent position in other xylanase molecules, at least one disulfide bridge, or a combination thereof. U.S. Pat. No. 7,314,743 discloses a modified xylanase having at least one substituted amino acid residue at a position corresponding to the *Trichoderma reesei* xylanase II amino acid sequence. WO 2007/115391 discloses a modified Family 11 xylanase enzyme comprising cysteine residues at positions 99 and 118 corresponding to the *Trichoderma reesei* xylanase II amino acid sequence to form an intramolecular disulfide bond.

The present invention provides variants of a xylanase with improved properties compared to its parent enzyme.

SUMMARY OF THE INVENTION

The present invention relates to variants of a GH Family 11 xylanase, comprising amino acid substitutions at one or more (e.g., several) positions corresponding to positions 120, 17, 24, 46, 49, 69, and 180 of SEQ ID NO: 2, wherein the variants have improved thermostability, thermoactivity, and/or altered pH activity profile.

The present invention relates to variants of a GH Family 11 xylanase, comprising amino acid substitutions at one or more (e.g., several) positions corresponding to positions 49, 55, 79, 82, 105, 155, and 215 of SEQ ID NO: 8, wherein the variants have improved thermostability, thermoactivity, and/or altered pH activity profile.

The present invention also relates to polynucleotides encoding the variants; nucleic acid constructs, vectors, and host cells comprising the polynucleotides; and methods of producing the variants.

The present invention further relates to methods of degrading a xylan-containing material comprising treating the material with such a variant.

The present invention also relates to methods for treating a pulp, comprising contacting the pulp with such a variant.

The present invention further relates to methods or producing xylose, comprising contacting a xylan-containing material with such a variant.

T120S+Q125A+I129E+T131N+Q162H+F180Y). Relative activity was calculated by dividing the activity at each temperature by the maximal activity.

Figure 7:
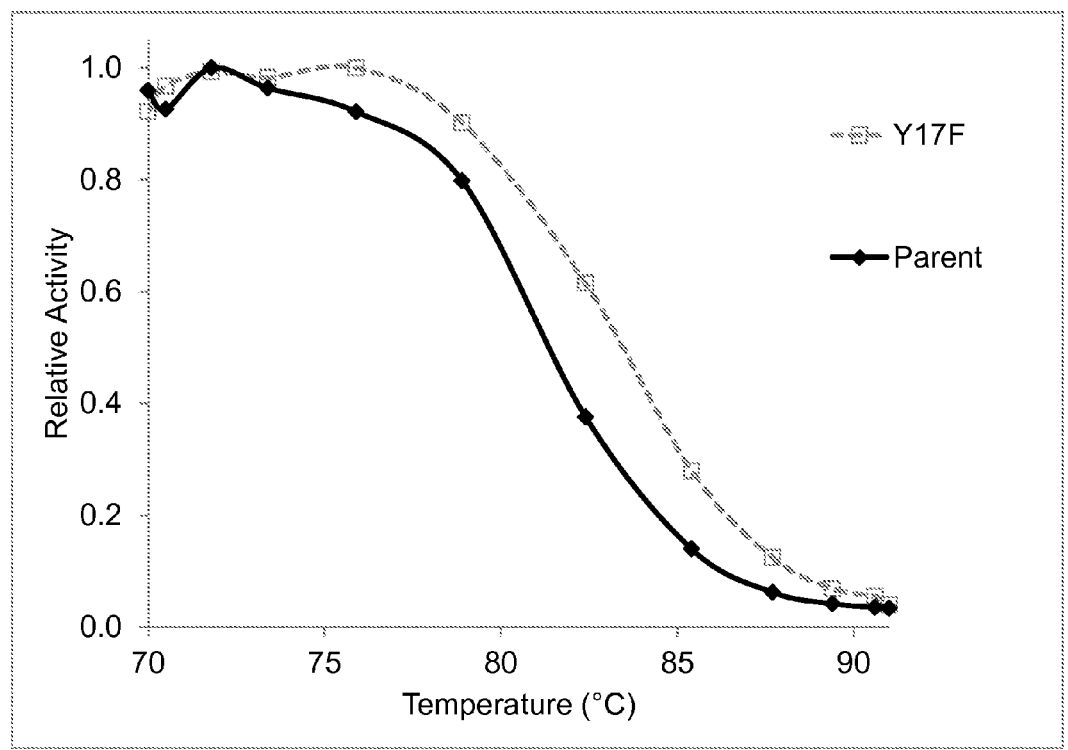

FIG. 7 shows the thermoactivity profiles for a parental GH11 xylanase (TrXyn2+N10D+N11D+G24C+Y27M+N29L+S40R+K58R+S75A+S99C+L105H+Y118C+T120S+Q125A+I129E+T131N+Q162H+F180Y) and a GH11 xylanase variant (TrXyn2+N10D+N11D+Y17F+G24C+Y27M+N29L+S40R+K58R+S75A+S99C+L105H+Y118C+T120S+Q125A+I129E+T131N+Q162H+F180Y). Relative activity was calculated by dividing the activity at each temperature by the maximal activity.

Figure 8:
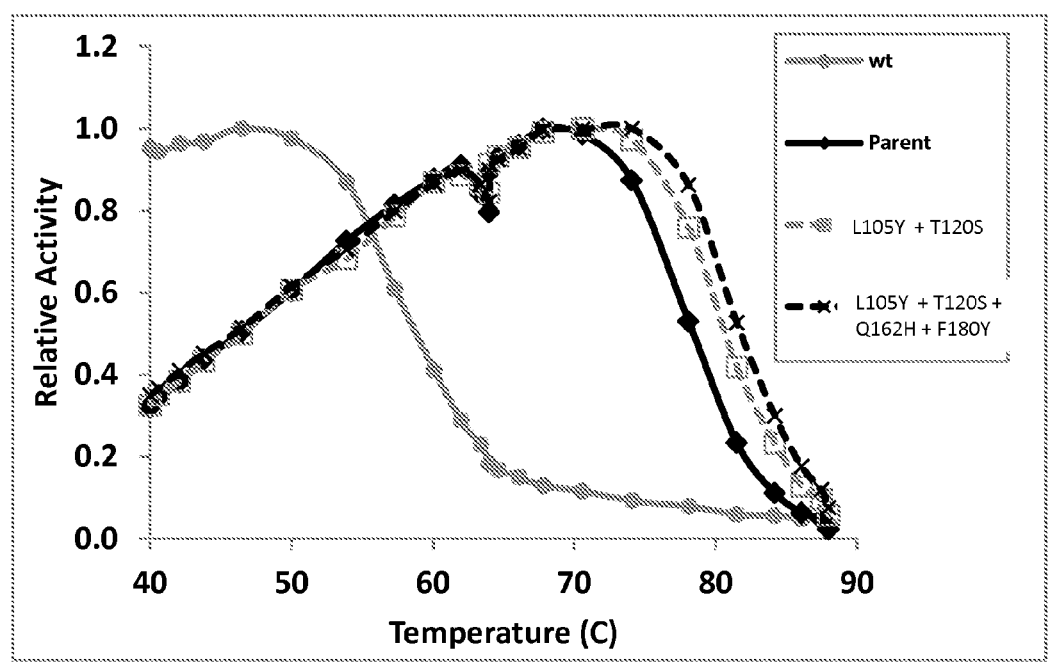

FIG. 8 shows the thermoactivity profiles for a wild-type GH11 xylanase (*T. reesei* xynII, "wt"), a parental GH11 xylanase (TrXyn2+N10D+N11D+Y27M+N29L+S40R+K58R+S75A+S99C+L105H+Y118C+Q125A+I129E+T131N) and two GH11 xylanase variants (TrXyn2+N10D+N11D+Y27M+N29L+S40R+K58R+S75A+S99C+L105Y+Y118C+T120S+Q125A+I129E+T131N and TrXyn2+N10D+N11D+Y27M+N29L+S40R+K58R+S75A+S99C+L105Y+Y118C+T120S+Q125A+I129E+T131N+Q162H+F180Y). Relative activity was calculated by dividing the activity at each temperature by the maximal activity.

Figure 9:
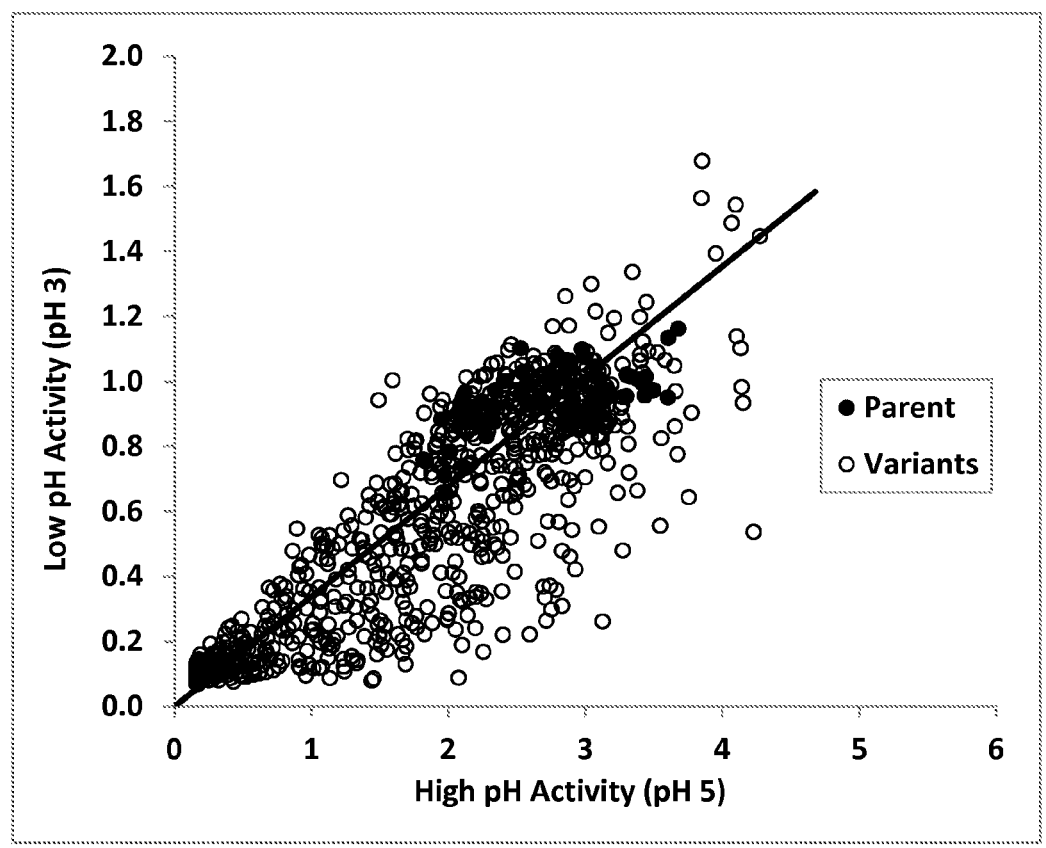

FIG. 9 shows altered pH activity profile data from one full round of screening. Plotted on the y-axis is xylanase activity at the low pH (pH 3) and plotted on the x-axis is xylanase activity at the high pH (pH 5) for GH11 xylanase variants and parental xylanase controls.

Figure 10:
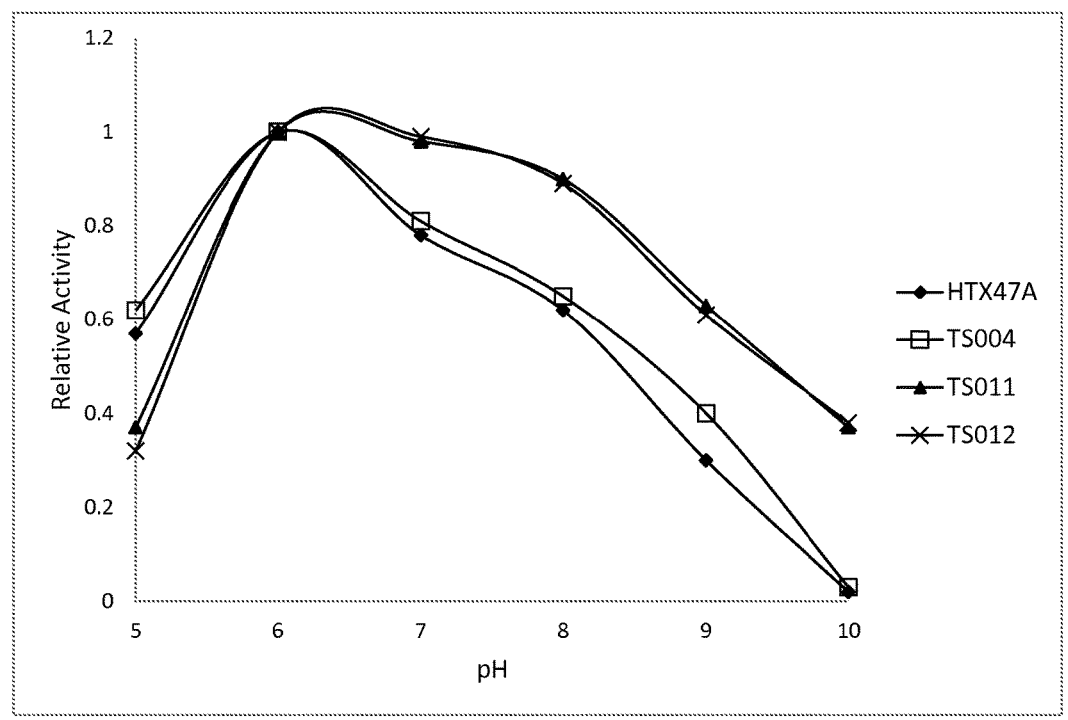

FIG. 10 shows the pH activity profiles for a parental GH11 xylanase (HTX47A) and three GH Family 11 xylanase variants (TS004, TS011, and TS012). Relative activity was calculated by dividing the activity at each temperature by the maximal activity.

DEFINITIONS

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity may be determined with 0.2% AZCL-arabinoxylan as substrate in 0.01% TRITON® X-100 and 200 mM sodium phosphate pH 6 at 37° C. and one unit of xylanase activity is defined as 1.0 µmole of azurine produced per minute at 37° C., pH 6 from 0.2% AZCL-arabinoxylan as substrate in 200 mM sodiumaltered pH phosphate pH 6. Examples 6 and 8 describe a xylanase assay which measures the release of reducing sugars from wheat arabinoxylan.

Hydrolysis of polysaccharides can also be monitored by chromatographic methods that separate and quantify soluble mono-, di- and oligo-saccharides released by the enzyme. A further method involves determining the change in viscosity with time as the enzyme acts on the substrate. In addition, soluble colorimetric substrates may be incorporated into agar-medium on which a host microbe expressing and secreting a parent or variant GH Family 11 xylanase is grown. In such an agar-plate assay, activity of the xylansae is detected as a coloured or colourless halo around the individual microbial colony expressing and secreting an active xylanase. The specific activity of a GH Family 11 xylanase is determined by measuring the activity of the enzyme, typically in units of amount of xylose or reducing sugar released per unit of time divided by the weight of the enzyme. For example, the specific activity may be determined in units of micromoles of xylose produced per minute per milligram of enzyme.

GH Family 11 Xylanase: As used herein, the term "Family 11 xylanase" or "GH11 xylanase" encompasses a xylanase that contains a glycohydrolase (GH) Family 11 catalytic domain. All Family 11 xylanase catalytic domains from bacterial and fungal sources share the same general molecular structure comprising mainly beta-sheets, turns and a single alpha helix. Alignment of the amino acid sequences of 82 Family 11 xylanases ranging in length from 173 to 220 amino acids and spanning a broad range of isoelectric points (pI 3.5 to 10.25), pH optima (2.0 to 8.0) and temperature optima (45° C. to 75° C.) identified highly conserved signature sequences in beta strands B5, B6, and B8 as well as in the alpha helix (Sapag et al., 2002). Furthermore, the secondary structure of Family 11 xylanases is highly conserved. Pairwise comparisons of the C-alpha atoms of ten Family 11 xylanase exhibiting from 31-97% identity in amino acid sequence using structural co-ordinates from the Protein Data Bank (PDB) showed that the root-mean-square deviation (rmsd) ranged from 0.6 to 1.4 Å (Hakulinen et al. 2003; incorporated herein by reference). Furthermore, all Family 11 xylanases contain two conserved glutamate residues at positions 86 and 177 (based on *Trichoderma reesei* xylanase II (TrX II, or Tr2) amino acid numbering), which are located on beta-strands B4 and B5 (Torronen & Rouvinen, 1995; Sapag et al., 2002, which are each incorporated herein by reference).

Given the highly conserved structure within the Family 11 xylanase, one skilled in the art can apply known methods, including the approaches outlined herein, to increase the thermoactivity and/or thermostability, or alter the pH activity profile, of any Family 11 xylanase. Non-limiting examples of Family 11 xylanases are presented in Sapag et al. (2002) and Hakulinen et al. (2003) and disclosed at the URL: cazy.org/fam/GH11.html, which are each incorporated herein by reference.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, birchwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylan degrading activity is preferably determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide that directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be RNA, messenger RNA or mRNA, genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, transcriptional terminator, and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has xylanase activity. In one aspect, a fragment contains at least 185 amino acid residues (e.g., amino acids 1-185 or 6-190 of SEQ ID NO: 2), at least 180 amino acid residues (e.g., amino acids 6-185 or 1-180 or 10-190 of SEQ ID NO: 2), or at least 170 amino acid residues (e.g., amino acids 10 to 180 of SEQ ID NO: 2).

High stringency conditions: The term "high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like, with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, thermal activity, thermostability, stability under storage conditions, specific activity, substrate binding, substrate cleavage, substrate specificity, catalytic efficiency, catalytic rate, pH activity, pH stability, substrate stability, surface properties, chemical stability, and oxidation stability.

Isolated: The term "isolated" means a substance in a form or environment which does not occur in nature. Non-limiting examples of isolated substances include (1) any non-naturally occurring substance, (2) any substance including, but not limited to, any enzyme, enzyme variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance; enrichment of the substance within a composition). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 190 of SEQ ID NO: 2 or amino acids 34-223 of SEQ ID NO: 3, as determined by N-terminal sequencing of the purified *T. reesei* Xyn2 protein (Saaraleinen et al., 1993, *Mol. Gen. Genet.* 241: 497-503). Analysis of the full-length amino acid sequence of SEQ ID NO: 3 using a program predicting signal peptides, e.g., SignalP (Nielsen et al., 1997, *Protein Engineering* 10: 1-6)] predicts a signal peptidase cleavage site between amino acids 19 and 20 of SEQ ID NO: 3. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having xylanase activity. In one aspect, the mature polypeptide coding sequence is nucleotides 100-272 and 381-777 of SEQ ID NO: 1. SEQ ID NO: 1 contains one intron consisting of nucleotides 273-380. Experimental evidence (Saaraleinen et al., 1993,) has determined that nucleotides 1 to 99 of SEQ ID NO: 1 encode a signal peptide. In another aspect, the mature polypeptide coding sequence is nucleotides 84-693 of SEQ ID NO: 7.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" or "mutated" refers to a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide, such that the control sequence directs expression of the coding sequence.

Parent or parental xylanase: The term "parent", "parent xylanase", or "parental xylanase" means a xylanase to which an alteration is made to produce the enzyme variants of the present invention. The parent may be a naturally occurring (wild-type) polypeptide or a variant or fragment thereof. In one aspect the parental xylanase is a *Trichoderma reesei* GH Family 11 xylanase. In another aspect, the parental *Trichoderma reesei* GH Family 11 xylanase is xylanase II having the amino acid sequence of SEQ ID NO: 2. In another aspect, the parental *Trichoderma reesei* GH Family 11 xylanase is a variant xylanase II having the amino acid sequence of SEQ ID NO: 4, containing the following amino acid substitutions N10H+Y27M+N29L+S75A+L105H+Q125A+I129E+N11D+S40R+K58R+S99C+Y118C+T131N. In another aspect, the parent xylanase comprises amino acids 28-231 of SEQ ID NO: 8. Other suitable parental GH Family 11 xylanases include, but are not limited to, the known GH Family 11 xylanases shown in Table 1.

TABLE 1

Examples of known Family 11 xylanases

| GenPept Accession No. | Organism |
|---|---|
| AAB29346.1 | *Trichoderma reesei* |
| ACF40831.1 | *Trichoderma harzianum* |
| EHK25808.1 | *Trichoderma virens* |
| AAP83925.1 | *Trichoderma viride* |
| EHK39428.1 | *Trichoderma atroviride* |
| EGO60109.1 | *Neurospora tetrasperma* |
| XP 957450.2 | *Neurospora crassa* |
| EFQ27362.1 | *Colletotrichum graminicola* |
| BAE71133.1 | *Penicillium citrinum* |
| CAD48749.1 | *Chaetomium thermophilum* |
| XP 003662402.1 | *Myceliophthora thermophila* |
| EXF79062.1 | *Colletotrichum fioriniae* |
| ESZ90255.1 | *Sclerotinia borealis* |
| EXG47004.1 | *Fusarium verticillioides* |
| AAG44994.1 | *Phanerochaete chrysosporium* |
| AAK27974.1 | *Fusarium oxysporum* |
| ADO14136.2 | *Podospora anserina* |
| XP 682634.1 | *Aspergillus nidulans* |
| AAZ03776.1 | *Botryotinia fuckeliana* |
| EIT80047.1 | *Aspergillus oryzae* |
| XP 001214121.1 | *Aspergillus terreus* |
| XP 001258363.1 | *Neosartotya fischeri* |
| ACI19073.1 | *Dictyoglucomus thermophilus* |
| AFN70714.1 | *Paenibacillus xylaniclasticus* |
| YP 008910560.1 | *Paenibacillus polymyxa* |
| WP 003519776.1 | *Clostridium thermocellum* |
| WP 003238262.1 | *Bacillus subtilis* |
| WP 002847764.1 | *Ruminococcus albus* |

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 555 nucleotides (e.g., nucleotides 100-272 and 381-762 or nucleotides 115-272 and 381-777 of SEQ ID NO: 1), at least 540 nucleotides (e.g., nucleotides 100-272 and 381-747, or nucleotides 115-272 and 381-762, or nucleotides 130-272 and 381-777 of SEQ ID NO: 1), or at least 510 nucleotides (e.g., nucleotides 130-272 and 381-747 SEQ ID NO: 1).

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the xylanase activity of the polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type xylanase: The term "wild-type" xylanase means a xylanase expressed by a naturally occurring microorganism, such as a bacterium, yeast, or filamentous fungus found in nature.

Conventions for Designation of Variants

For purposes of the present invention, the mature polypeptide disclosed in SEQ ID NO: 2 (*T. reesei* Xyn2 or TrXyn2) is used to determine the corresponding amino acid residue in another GH Family 11 xylanase. The amino acid sequence of another GH Family 11 xylanase is aligned with the mature polypeptide disclosed in SEQ ID NO: 2 and, based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another GH Family 11 xylanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other GH Family 11 xylanase has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as Gen-THREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr26Ala" or "T26A". Multiple mutations are separated by addition marks ("+"), e.g., "Gly20Arg+Ser41Phe" or "G20R+S41F", representing substitutions at positions 20 and 41 of glycine (G) with arginine (R) and serine (S) with phenylalanine (F), respectively.

Deletions. For an amino acid deletion, the following nomenclature is used: Original amino acid, position, *. Accordingly, the deletion of glycine at position 175 is designated as "Gly175*" or "G175*". Multiple deletions are separated by addition marks ("+"), e.g., "Gly175*+Ser41*" or "G175*+S41*".

Insertions. For an amino acid insertion, the following nomenclature is used: Original amino acid, position, original amino acid, inserted amino acid. Accordingly the insertion of lysine after glycine at position 195 is designated "Gly175GlyLys" or "G175GK". An insertion of multiple amino acids is designated [Original amino acid, position, original amino acid, inserted amino acid #1, inserted amino acid #2; etc.]. For example, the insertion of lysine and alanine after glycine at position 175 is indicated as "Gly175GlyLysAla" or "G175GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 175 | 175 175a 175b |
| G | G-K-A |

Multiple amino acid substitutions. Variants comprising multiple amino acid substitutions are separated by addition marks ("+"), e.g., "Arg170Tyr+Gly175Glu" or "R170Y+G175E" representing a substitution of arginine and glycine at positions 170 and 175 with tyrosine and glutamic acid, respectively.

Different amino acid substitutions. Where different amino acid substitutions can be introduced at a position, the different amino acid substitutions are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to variants of GH Family 11 xylanases, comprising a substitution at one or more (e.g., several) positions corresponding to positions of the mature polypeptide of SEQ ID NO: 2, wherein the variant has xylanase activity.

Variants

The present invention provides variants of GH Family 11 xylanases, comprising a substitution at one or more (e.g., several) positions corresponding to positions 120, 17, 24, 46, 49, 69, and 180 of the polypeptide of SEQ ID NO: 2 or SEQ ID NO: 4, wherein the variant has xylanase activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent xylanase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2, SEQ ID NO: 4, or amino acids 28-231 of SEQ ID NO: 8.

In one aspect, the number of amino acid substitutions in the variants of the present invention is 1-20, e.g., 1-10 and 1-5, such as 1, 2, 3, 4, 5, 6, 7, 8, 9, 10, 11, 12, 13, 14, 15, 16, 17, 18, 19, or 20 amino acid substitutions.

The amino acid changes may be of a minor nature, that is conservative amino acid substitutions or insertions that do not significantly affect the folding and/or activity of the protein; small deletions, typically of 1-20 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermostability and/or thermal activity of the polypeptide, change the pH activity profile, and the like. For example, the variants may comprise a Thr to Ser at position 120 of SEQ ID NO: 2 or SEQ ID NO: 4, a Tyr to Phe substitution at position 17 of SEQ ID NO: 2 or SEQ ID NO: 4, a Gly to Cys substitution at position 24 of SEQ ID NO: 2 or SEQ ID NO: 4, a Val to Ile substitution at position 46 of SEQ ID NO: 2 or SEQ ID NO: 4, a Lys to Met or a Lys to Glu at position 49 of SEQ ID NO: 2 or SEQ ID NO: 4, an Asn to Asp at position 69, and a Phe to Tyr substitution at position 180 of SEQ ID NO: 2 or SEQ ID NO: 4.

In another aspect, a variant comprises an amino acid substitution at one or more (e.g., several) positions corresponding to positions 120, 17, 24, 46, 49, 69, and 180 of SEQ ID NO: 2. In another aspect, a variant comprises an amino acid substitution at two positions corresponding to any of positions 120, 17, 24, 46, 49, 69, and 180 of SEQ ID NO: 2. In another aspect, a variant comprises an amino acid substitution at three positions corresponding to any of positions 120, 17, 24, 46, 49, 69, and 180 of SEQ ID NO: 2. In another aspect, a variant comprises an amino acid substitution at four positions corresponding to any of positions 120, 17, 24, 46, 49, 69, and 180 of SEQ ID NO: 2. In another aspect, a variant comprises an amino acid substitution at five positions corresponding to any of positions 120, 17, 24, 46, 49, 69, and 180 of SEQ ID NO: 2. In another aspect, a variant comprises an amino acid substitution at six positions corresponding to any of positions 120, 17, 24, 46, 49, 69, and 180 of SEQ ID NO: 2. In another aspect, a variant comprises an amino acid substitution at each position corresponding to positions 120, 17, 24, 46, 49, 69, and 180 of SEQ ID NO: 2.

In another aspect, the variant comprises or consists of an amino acid substitution at a position corresponding to position 120 of SEQ ID NO: 2. In another aspect, the amino acid at a position corresponding to position 120 is substituted with Ala, Arg, Asn, Asp, Cys, Gln, Glu, Gly, His, Ile, Leu, Lys, Met, Phe, Pro, Ser, Trp, Tyr, or Val, preferably with Ser.

In another aspect, the variant comprises or consists of the substitution T120S of SEQ ID NO: 2 or SEQ ID NO: 4.

In another aspect, the variant comprises or consists of an amino acid substitution at a position corresponding to position 17 of SEQ ID NO: 2. In another aspect, the amino acid at a position corresponding to position 17 is substituted with Ala, Arg, Asn, Asp, Cys, Gln, Glu, Gly, His, Ile, Leu, Lys, Met, Phe, Pro, Ser, Thr, Trp, or Val, preferably with Ile. In another aspect, the variant comprises or consists of the substitution Y17F of SEQ ID NO: 2 or SEQ ID NO: 4.

In another aspect, the variant comprises or consists of an amino acid substitution at a position corresponding to position 24 of SEQ ID NO: 2. In another aspect, the amino acid at a position corresponding to position 24 is substituted with Ala, Arg, Asn, Asp, Cys, Gln, Glu, His, Ile, Leu, Lys, Met, Phe, Pro, Ser, Thr, Trp, Tyr, or Val, preferably with Cys. In another aspect, the variant comprises or consists of the substitution G24C of SEQ ID NO: 2 or SEQ ID NO: 4.

In another aspect, the variant comprises or consists of an amino acid substitution at a position corresponding to position 46 of SEQ ID NO: 2. In another aspect, the amino acid at a position corresponding to position 46 is substituted with Ala, Arg, Asn, Asp, Cys, Gln, Glu, Gly, His, Ile, Leu, Lys, Met, Phe, Pro, Ser, Thr, Trp, or Tyr, preferably with Ile. In another aspect, the variant comprises or consists of the substitution V46I of SEQ ID NO: 2 or SEQ ID NO: 4.

In another aspect, the variant comprises or consists of an amino acid substitution at a position corresponding to position 49 of SEQ ID NO: 2. In another aspect, the amino acid at a position corresponding to position 49 is substituted with Ala, Arg, Asn, Asp, Cys, Gln, Glu, Gly, His, Ile, Leu, Met, Phe, Pro, Ser, Thr, Trp, Tyr, or Val, preferably with Met or Glu. In another aspect, the variant comprises or consists of the substitution K49M of SEQ ID NO: 2 or SEQ ID NO: 4. In yet another aspect, the variant comprises or consists of the substitution K49E of SEQ ID NO: 2 or SEQ ID NO: 4.

In another aspect, the variant comprises or consists of an amino acid substitution at a position corresponding to position 69 of SEQ ID NO: 2. In another aspect, the amino acid at a position corresponding to position 69 is substituted with Ala, Arg, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution N69D of SEQ ID NO: 2 or SEQ ID NO: 4.

In another aspect, the variant comprises or consists of an amino acid substitution at a position corresponding to position 180 of SEQ ID NO: 2. In another aspect, the amino acid at a position corresponding to position 180 is substituted with Ala, Arg, Asn, Asp, Cys, Gln, Glu, Gly, His, Ile, Leu, Lys, Met, Pro, Ser, Thr, Trp, Tyr, or Val, preferably with Tyr. In another aspect, the variant comprises or consists of the substitution F180Y of SEQ ID NO: 2 or SEQ ID NO: 4.

In another aspect, the variant further comprises or consists of an amino acid substitution at a position corresponding to position 10 of SEQ ID NO: 2. In another aspect, the amino acid at a position corresponding to position 10 is substituted with Ala, Arg, Asp, Cys, Gln, Glu, Gly, His, Ile, Leu, Lys, Met, Phe, Pro, Ser, Thr, Trp, Tyr, or Val, preferably with Gln, Tyr, or Arg. In another aspect, the variant comprises or consists of the substitution N10Q, N10Y, or N10R of SEQ ID NO: 2.

In another aspect, the variant further comprises or consists of an amino acid substitution at a position corresponding to position 105 of SEQ ID NO: 2. In another aspect, the amino acid at a position corresponding to position 105 is substituted with Ala, Arg, Asp, Cys, Gln, Glu, Gly, His, Ile, Lys, Met, Phe, Pro, Ser, Thr, Trp, Tyr, or Val, preferably with Tyr.

In another aspect, the variant comprises or consists of the substitution L105Y of SEQ ID NO: 2.

In another aspect, the variant comprises or consists of amino acid substitutions at positions corresponding to positions 120 and 17 of SEQ ID NO: 2, such as those described above.

In another aspect, the variant comprises or consists of amino acid substitutions at positions corresponding to positions 120 and 24 of SEQ ID NO: 2, such as those described above.

In another aspect, the variant comprises or consists of amino acid substitutions at positions corresponding to positions 120 and 46 of SEQ ID NO: 2, such as those described above.

In another aspect, the variant comprises or consists of amino acid substitutions at positions corresponding to positions 120 and 49 of SEQ ID NO: 2, such as those described above.

In another aspect, the variant comprises or consists of amino acid substitutions at positions corresponding to positions 120 and 69 of SEQ ID NO: 2, such as those described above.

In another aspect, the variant comprises or consists of amino acid substitutions at positions corresponding to positions 120 and 180 of SEQ ID NO: 2, such as those described above.

In another aspect, the variant comprises or consists of amino acid substitutions at positions corresponding to positions 17 and 24 of SEQ ID NO: 2, such as those described above.

In another aspect, the variant comprises or consists of amino acid substitutions at positions corresponding to positions 17 and 46 of SEQ ID NO: 2, such as those described above.

In another aspect, the variant comprises or consists of amino acid substitutions at positions corresponding to positions 17 and 49 of SEQ ID NO: 2, such as those described above.

In another aspect, the variant comprises or consists of amino acid substitutions at positions corresponding to positions 17 and 69 of SEQ ID NO: 2, such as those described above.

In another aspect, the variant comprises or consists of amino acid substitutions at positions corresponding to positions 17 and 180 of SEQ ID NO: 2, such as those described above.

In another aspect, the variant comprises or consists of amino acid substitutions at positions corresponding to positions 24 and 46 of SEQ ID NO: 2, such as those described above.

In another aspect, the variant comprises or consists of amino acid substitutions at positions corresponding to positions 24 and 49 of SEQ ID NO: 2, such as those described above.

In another aspect, the variant comprises or consists of amino acid substitutions at positions corresponding to positions 24 and 69 of SEQ ID NO: 2, such as those described above.

In another aspect, the variant comprises or consists of amino acid substitutions at positions corresponding to positions 24 and 180 of SEQ ID NO: 2, such as those described above.

In another aspect, the variant comprises or consists of amino acid substitutions at positions corresponding to positions 46 and 49 of SEQ ID NO: 2, such as those described above.

In another aspect, the variant comprises or consists of amino acid substitutions at positions corresponding to positions 46 and 69 of SEQ ID NO: 2, such as those described above.

In another aspect, the variant comprises or consists of amino acid substitutions at positions corresponding to positions 46 and 180 of SEQ ID NO: 2, such as those described above.

In another aspect, the variant comprises or consists of amino acid substitutions at positions corresponding to positions 49 and 69 of SEQ ID NO: 2, such as those described above.

In another aspect, the variant comprises or consists of amino acid substitutions at positions corresponding to positions 49 and 180 of SEQ ID NO: 2, such as those described above.

In another aspect, the variant comprises or consists of amino acid substitutions at positions corresponding to positions 69 and 180 of SEQ ID NO: 2, such as those described above.

In another aspect, the variant comprises or consists of amino acid substitutions at positions corresponding to positions 120, 17, and 24 of SEQ ID NO: 2, such as those described above.

In another aspect, the variant comprises or consists of amino acid substitutions at positions corresponding to positions 120, 17, and 46 of SEQ ID NO: 2, such as those described above.

In another aspect, the variant comprises or consists of amino acid substitutions at positions corresponding to positions 120, 17, and 49 of SEQ ID NO: 2, such as those described above.

In another aspect, the variant comprises or consists of amino acid substitutions at positions corresponding to positions 120, 17, and 69 of SEQ ID NO: 2, such as those described above.

In another aspect, the variant comprises or consists of amino acid substitutions at positions corresponding to positions 120, 17, and 180 of SEQ ID NO: 2, such as those described above.

In another aspect, the variant comprises or consists of amino acid substitutions at positions corresponding to positions 120, 24, and 46 of SEQ ID NO: 2, such as those described above.

In another aspect, the variant comprises or consists of amino acid substitutions at positions corresponding to positions 120, 24, and 49 of SEQ ID NO: 2, such as those described above.

In another aspect, the variant comprises or consists of amino acid substitutions at positions corresponding to positions 120, 24, and 69 of SEQ ID NO: 2, such as those described above.

In another aspect, the variant comprises or consists of amino acid substitutions at positions corresponding to positions 120, 24, and 180 of SEQ ID NO: 2, such as those described above.

In another aspect, the variant comprises or consists of amino acid substitutions at positions corresponding to positions 120, 46, and 49 of SEQ ID NO: 2, such as those described above.

In another aspect, the variant comprises or consists of amino acid substitutions at positions corresponding to positions 120, 46, and 69 of SEQ ID NO: 2, such as those described above.

In another aspect, the variant comprises or consists of amino acid substitutions at positions corresponding to positions 120, 46, and 180 of SEQ ID NO: 2, such as those described above.

In another aspect, the variant comprises or consists of amino acid substitutions at positions corresponding to positions 120, 49, and 69 of SEQ ID NO: 2, such as those described above.

In another aspect, the variant comprises or consists of amino acid substitutions at positions corresponding to positions 120, 49, and 180 of SEQ ID NO: 2, such as those described above.

In another aspect, the variant comprises or consists of amino acid substitutions at positions corresponding to positions 120, 69, and 180 of SEQ ID NO: 2, such as those described above.

In another aspect, the variant comprises or consists of amino acid substitutions at positions corresponding to positions 17, 24, and 46 of SEQ ID NO: 2, such as those described above.

In another aspect, the variant comprises or consists of amino acid substitutions at positions corresponding to positions 17, 24, and 49 of SEQ ID NO: 2, such as those described above.

In another aspect, the variant comprises or consists of amino acid substitutions at positions corresponding to positions 17, 24, and 69 of SEQ ID NO: 2, such as those described above.

In another aspect, the variant comprises or consists of amino acid substitutions at positions corresponding to positions 17, 24, and 180 of SEQ ID NO: 2, such as those described above.

In another aspect, the variant comprises or consists of amino acid substitutions at positions corresponding to positions 17, 46, and 49 of SEQ ID NO: 2, such as those described above.

In another aspect, the variant comprises or consists of amino acid substitutions at positions corresponding to positions 17, 46, and 69 of SEQ ID NO: 2, such as those described above.

In another aspect, the variant comprises or consists of amino acid substitutions at positions corresponding to positions 17, 46, and 180 of SEQ ID NO: 2, such as those described above.

In another aspect, the variant comprises or consists of amino acid substitutions at positions corresponding to positions 17, 49, and 69 of SEQ ID NO: 2, such as those described above.

In another aspect, the variant comprises or consists of amino acid substitutions at positions corresponding to positions 17, 49, and 180 of SEQ ID NO: 2, such as those described above.

In another aspect, the variant comprises or consists of amino acid substitutions at positions corresponding to positions 17, 69, and 180 of SEQ ID NO: 2, such as those described above.

In another aspect, the variant comprises or consists of amino acid substitutions at positions corresponding to positions 24, 46, and 49 of SEQ ID NO: 2, such as those described above.

In another aspect, the variant comprises or consists of amino acid substitutions at positions corresponding to positions 24, 46, and 69 of SEQ ID NO: 2, such as those described above.

In another aspect, the variant comprises or consists of amino acid substitutions at positions corresponding to positions 24, 46, and 180 of SEQ ID NO: 2, such as those described above.

In another aspect, the variant comprises or consists of amino acid substitutions at positions corresponding to positions 24, 49, and 69 of SEQ ID NO: 2, such as those described above.

In another aspect, the variant comprises or consists of amino acid substitutions at positions corresponding to positions 24, 49, and 180 of SEQ ID NO: 2, such as those described above.

In another aspect, the variant comprises or consists of amino acid substitutions at positions corresponding to positions 24, 69, and 180 of SEQ ID NO: 2, such as those described above.

In another aspect, the variant comprises or consists of amino acid substitutions at positions corresponding to positions 46, 49, and 69 of SEQ ID NO: 2, such as those described above.

In another aspect, the variant comprises or consists of amino acid substitutions at positions corresponding to positions 46, 49, and 180 of SEQ ID NO: 2, such as those described above.

In another aspect, the variant comprises or consists of amino acid substitutions at positions corresponding to positions 120, 17, 24, and 46 of SEQ ID NO: 2, such as those described above.

In another aspect, the variant comprises or consists of amino acid substitutions at positions corresponding to positions 120, 17, 24, and 49 of SEQ ID NO: 2, such as those described above.

In another aspect, the variant comprises or consists of amino acid substitutions at positions corresponding to positions 120, 17, 24, and 69 of SEQ ID NO: 2, such as those described above.

In another aspect, the variant comprises or consists of amino acid substitutions at positions corresponding to positions 120, 17, 24, and 180 of SEQ ID NO: 2, such as those described above.

In another aspect, the variant comprises or consists of amino acid substitutions at positions corresponding to positions 120, 24, 46, and 49 of SEQ ID NO: 2, such as those described above.

In another aspect, the variant comprises or consists of amino acid substitutions at positions corresponding to positions 120, 24, 46, and 69 of SEQ ID NO: 2, such as those described above.

In another aspect, the variant comprises or consists of amino acid substitutions at positions corresponding to positions 120, 24, 46, and 180 of SEQ ID NO: 2, such as those described above.

In another aspect, the variant comprises or consists of amino acid substitutions at positions corresponding to positions 120, 46, 49, and 69 of SEQ ID NO: 2, such as those described above.

In another aspect, the variant comprises or consists of amino acid substitutions at positions corresponding to positions 120, 46, 49, and 180 of SEQ ID NO: 2, such as those described above.

In another aspect, the variant comprises or consists of amino acid substitutions at positions corresponding to positions 120, 49, 69, and 180 of SEQ ID NO: 2, such as those described above.

In another aspect, the variant comprises or consists of amino acid substitutions at positions corresponding to positions 17, 24, 46, and 49 of SEQ ID NO: 2, such as those described above.

In another aspect, the variant comprises or consists of amino acid substitutions at positions corresponding to positions 17, 24, 46, and 69 of SEQ ID NO: 2, such as those described above.

In another aspect, the variant comprises or consists of amino acid substitutions at positions corresponding to positions 17, 24, 46, and 180 of SEQ ID NO: 2, such as those described above.

In another aspect, the variant comprises or consists of amino acid substitutions at positions corresponding to positions 17, 46, 49, and 69 of SEQ ID NO: 2, such as those described above.

In another aspect, the variant comprises or consists of amino acid substitutions at positions corresponding to positions 17, 46, 49, and 180 of SEQ ID NO: 2, such as those described above.

In another aspect, the variant comprises or consists of amino acid substitutions at positions corresponding to positions 17, 49, 69, and 180 of SEQ ID NO: 2, such as those described above.

In another aspect, the variant comprises or consists of amino acid substitutions at positions corresponding to positions 24, 46, 49, and 69 of SEQ ID NO: 2, such as those described above.

In another aspect, the variant comprises or consists of amino acid substitutions at positions corresponding to positions 24, 46, 49, and 180 of SEQ ID NO: 2, such as those described above.

In another aspect, the variant comprises or consists of amino acid substitutions at positions corresponding to positions 24, 49, 69, and 180 of SEQ ID NO: 2, such as those described above.

In another aspect, the variant further comprises or consists of an amino acid substitution at positions corresponding to positions 10, 27 and 29 of SEQ ID NO: 2. In another aspect, the amino acid at a position corresponding to position 10 is substituted with Ala, Arg, Asn, Asp, Cys, Gln, Glu, Gly, His, Ile, Leu, Lys, Met, Phe, Pro, Ser, Thr, Trp, or Val, preferably with His; the amino acid at a position corresponding to position 27 is substituted with Ala, Arg, Asn, Asp, Cys, Gln, Glu, Gly, His, Ile, Leu, Lys, Met, Phe, Pro, Ser, Thr, Trp, or Val, preferably with Met; and the amino acid at a position corresponding to position 29 is substituted with Ala, Arg, Asp, Cys, Gln, Glu, Gly, His, Ile, Leu, Lys, Met, Phe, Pro, Ser, Thr, Trp, Tyr, or Val, preferably with Leu. In another aspect, the variant further comprises or consists of the substitutions N10H, Y27M and N29L of SEQ ID NO: 2.

In another aspect, the variant further comprises or consists of an amino acid substitution at positions corresponding to positions 75, 125, and 129 of SEQ ID NO: 2. In another aspect, the amino acid at a position corresponding to position 75 is substituted with Ala, Arg, Asn, Asp, Cys, Gln, Glu, Gly, His, Ile, Leu, Lys, Met, Phe, Pro, Thr, Trp, Tyr, or Val, preferably with Ala; the amino acid at a position corresponding to position 125 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala; and the amino acid at a position corresponding to position 129 is substituted with Ala, Arg, Asn, Asp, Cys, Gln, Glu, Gly, His, Leu, Lys, Met, Phe, Pro, Ser, Thr, Trp, Tyr, or Val, preferably with Glu. In another aspect, the variant further comprises or consists of the substitutions S75A, Q125A and I129E of SEQ ID NO: 2.

In another aspect, the variant further comprises or consists of an amino acid substitution at positions corresponding to positions 11, 40 and 58 of SEQ ID NO: 2. In another aspect, the amino acid at a position corresponding to position 11 is substituted with Ala, Arg, Asp, Cys, Gln, Glu, Gly, His, Ile, Leu, Lys, Met, Phe, Pro, Ser, Thr, Trp, Tyr, or Val, preferably with Asp; the amino acid at a position corresponding to position 40 is substituted with Ala, Arg, Asn, Asp, Cys, Gln, Glu, Gly, His, Ile, Leu, Lys, Met, Phe, Pro, Thr, Trp, Tyr, or Val, preferably with Arg; and the amino acid at a position corresponding to position 58 is substituted with Ala, Arg, Asn, Asp, Cys, Gln, Glu, Gly, His, Ile, Leu, Met, Phe, Pro, Ser, Thr, Trp, Tyr, or Val, preferably with Arg. In another aspect, the variant further comprises or consists of the substitutions N11D, S40R, and K58R of the mature polypeptide of SEQ ID NO: 2.

In another aspect, the variant further comprises or consists of an amino acid substitution at one or both positions corresponding to positions 99 and 118 of SEQ ID NO: 2. In another aspect, the amino acid at one or both positions corresponding to position 99 and 118 is substituted with Cys. In another aspect, the variant further comprises or consists of the substitutions S99C and Y118C of SEQ ID NO: 2.

In another aspect, the variant further comprises or consists of an amino acid substitution at a position corresponding to position 131 of SEQ ID NO: 2. In another aspect, the amino acid at a position corresponding to position 131 is substituted with Asn. In another aspect, the variant further comprises or consists of the substitution T131N of SEQ ID NO: 2.

In another aspect, the variant further comprises or consists of an amino acid substitution at a position corresponding to position 162 of SEQ ID NO: 2 or SEQ ID NO: 4. In another aspect, the amino acid at a position corresponding to position 162 is substituted with His. In another aspect, the variant further comprises or consists of the substitution Q162H of SEQ ID NO: 2 or SEQ ID NO: 4.

In another aspect, the variant comprises or consists of one or more (e.g., several) substitutions selected from the group consisting of T120S, Y17F, G24C, V46I, K49M or K49E, N69D and F180Y.

In another aspect, the variant comprises or consists of the substitutions Y17F+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions G24C+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or lower pH activity profile compared to the GH11 xylanase of SEQ ID NO: 2 or SEQ ID NO: 4.

In another aspect, the variant comprises or consists of the substitutions V46I+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions K49M+T120S or K49E+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions N69D+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions T120S+F180Y of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+V46I of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions G24C+V46I of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+V46I+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions G24C+V46I+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+L105Y+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+L105Y+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+K49M+L105Y+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+K49E+L105Y+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+K49M+N69D+L105Y+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+K49E+N69D+L105Y+T120S of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+K49M+N69D+L105Y+T120S+F180Y of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions Y17F+G24C+V46I+K49E+N69D+L105Y+T120S+F180Y of the polypeptide of SEQ ID NO: 2 or SEQ ID NO: 4, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 or to SEQ ID NO: 4 and xylanase activity, and further the variant has improved thermostability, thermal activity or altered pH activity profile compared to the GH11 xylanase of SEQ ID NO: 2 or SEQ ID NO: 4.

In another aspect, the variant comprises or consists of the substitutions N10H+Y17F+Y27M+N29L+G24C+V46I+K49M+N69D+L105Y+T120S+F180Y+of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+Y17F+G24C+Y27M+N29L+V46I+K49E+N69D+L105Y+T120S of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+Y17F+G24C+Y27M+N29L+V46I+K49M+N69D+S75A+L105Y+T120S+Q125A+I129E+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+Y17F+G24C+Y27M+N29L+V46I+K49E+N69D+S75A+L105Y+T120S+Q125A+I129E+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11D+Y17F+G24C+Y27M+N29L+S40R+V46I+K49M+K58R+N69D+S75A+L105Y+T120S+Q125A+I129E+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11 D+Y17F+G24C+Y27M+N29L+S40R+V46I+K49E+K58R+N69D+S75A+L105Y+T120S+Q125A+I129E+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11D+Y17F+G24C+Y27M+N29L+S40R+V46I+K49M+K58R+N69D+S75A+S99C+L105Y+Y118C+T120S+Q125A+I129E+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11D+Y17F+G24C+Y27M+N29L+S40R+V46I+K49E+K58R+N69D+S75A+S99C+L105Y+Y118C+T120S+Q125A+I129E+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11 D+Y17F+G24C+Y27M+N29L+S40R+V46I+K49M+K58R+N69D+S75A+S99C+L105Y+Y118C+T120S+Q125A+I129E+T131N+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11D+Y17F+G24C+Y27M+N29L+S40R+V46I+K49E+K58R+N69D+S75A+S99C+L105Y+Y118C+T120S+Q125A+I129E+T131N+F180Y+of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11D+Y17F+G24C+Y27M+N29L+S40R+V46I+K49M+K58R+N69D+S75A+S99C+L105Y+Y118C+T120S+Q125A+I129E+T131N+Q162H+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

In another aspect, the variant comprises or consists of the substitutions N10H+N11D+Y17F+G24C+Y27M+N29L+S40R+V46I+K49E+K58R+N69D+S75A+S99C+L105Y+Y118C+T120S+Q125A+I129E+T131N+Q162H+F180Y of the polypeptide of SEQ ID NO: 2, and exhibits at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO: 2 and xylanase activity, and further the variant has improved thermostability, thermal activity or altered pH activity profile compared to the GH11 xylanase of SEQ ID NO: 2.

Additional mutations, other than those described above, may be introduced into the GH Family 11 xylanase, provided that such mutations do not significantly compromise the structure and function of the enzyme. As would be appreciated by those of ordinary skill in the art, but without being limiting in any manner, additional mutations may be introduced in regions of low sequence conservation among GH Family 11 xylanases, which can be identified by aligning the amino acid sequences GH Family 11 xylanases. The amino acid sequence alignment information can be used as guidance by those of ordinary skill in the art when introducing an additional mutation(s) at positions other than 120, 17, 24, 46, 49, 69 and 180 including, but not limited to, positions corresponding to positions 10, 11, 27, 29, 40, 58, 99, 105, 118, 125, 129, 131 and 162 of SEQ ID NO: 2.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for enzyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids in *T. reesei* xylanase II (Xyn2, Xyn II or Xyn 11B) having the amino acid sequence of SEQ ID NO: 2 include the catalytic glutamatic acid residues at position 86 and 177, E86 and E177 (Saaraleinen et al 1993). Other amino acids in *T. reesei* xylanase II (Xyn2, Xyn II or Xyn 11B), having the amino acid sequence of SEQ ID NO: 2, that are highly conserved among Family 11 xylanases include, but are not limited to, tryptophan at position 39 (W39), glycine at position 50 (G50), tyrosine-glycine-tryptophan (YGW) at positions 77-79, tyrosine-tyrosine-isoleucine-valine (YYIV) at positions 87-90, tyrosine at position 115 (Y115), proline at position 126 (P126), serine at position 127 (S127), phenylalanine at position 134 (F134), glutamine at position 136 (Q136), serine-valine-arginine at positions 139-141, histidine at position 155 (H155), tryptophan at position 159 (W159) and glycine at position 163 (G163).

The variants may consist of 170 to 190 amino acids, e.g., 180 to 190, and 185 to 190 amino acids, or any number of amino acids therebetween.

In an embodiment, the variant has improved thermal activity compared to the parent xylanase. Improved thermal activity of the variant compared to the parent xylanase may be determined using the method described in Example 7. In another embodiment, the variant has improved thermostability compared to the parent xylanase.

In other embodiments, the variant may be further improved compared to the parent xylanase in one or more of the following properties: improved stability under storage conditions, specific activity substrate binding, substrate cleavage, substrate specificity. catalytic efficiency, catalytic rate, pH activity, pH stability, substrate stability, surface properties, chemical stability, or oxidation stability.

Parent GH Family 11 Xylanases

The parent xylanase may be (a) a polypeptide having at least 60% sequence identity to the polypeptide of SEQ ID NO: 2, SEQ ID NO: 4, or amino acids 28-231 of SEQ ID NO: 8; (b) a polypeptide encoded by a polynucleotide that hybridizes under low stringency conditions with (i) the mature polypeptide coding sequence of SEQ ID NO: 1 or SEQ ID NO: 7, (ii) the cDNA sequence thereof, or (iii) the full-length complement of (i) or (ii); or (c) a polypeptide encoded by a polynucleotide having at least 60% sequence identity to the mature polypeptide coding sequence of SEQ ID NO: 1 or SEQ ID NO: 7.

In an aspect, the parent has a sequence identity to the polypeptide of SEQ ID NO: 2, SEQ ID NO: 4, or amino acids 28-231 of SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which has xylanase activity. In one aspect, the amino acid sequence of the parent differs by up to 20 amino acids, e.g., 1, 2, 3, 4, 5, 6, 7, 8, 9, 10, 11, 12, 13, 14, 15, 16, 17, 18, 19 or 20 amino acids from the polypeptide of SEQ ID NO: 2, SEQ ID NO: 4, SEQ ID NO: 4, or amino acids 28-231 of SEQ ID NO: 8.

In another aspect, the parent comprises or consists of the polypeptide of SEQ ID NO: 2. In another aspect, the parent comprises or consists of the polypeptide of SEQ ID NO: 4. In another aspect, the parent comprises or consists of amino acids 28-213 of SEQ ID NO: 8. In another aspect, the parent comprises or consists of the mature polypeptide of SEQ ID NO: 3. In another aspect, the parent comprises or consists of amino acids 23 to 418 of SEQ ID NO: 3.

In another aspect, the parent is a fragment of the polypeptide of SEQ ID NO: 2, SEQ ID NO: 4, or amino acids 28-213 of SEQ ID NO: 8 containing at least 170 amino acid residues, e.g., at least 180 or at least 185 amino acid residues.

In another embodiment, the parent is an allelic variant of the polypeptide of SEQ ID NO: 2, SEQ ID NO: 4, or amino acids 28-213 of SEQ ID NO: 8.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1 or SEQ ID NO: 7, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1 or SEQ ID NO: 7, or a subsequence thereof, as well as the polypeptide of SEQ ID NO: 2, SEQ ID NO: 4, or amino acids 28-213 of SEQ ID NO: 8, or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length.

Preferably, the nucleic acid probe is at least 100 nucleotides in length, e.g., at least 200 nucleotides, at least 300 nucleotides, at least 400 nucleotides, or at least 500 nucleotides. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or SEQ ID No: 7, or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID No: 7; (ii) the mature polypeptide coding sequence of SEQ ID NO: 1 or SEQ ID No: 7; (iii) the cDNA sequence thereof]; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe comprises nucleotides 100-272 and 381-777 of SEQ ID NO: 1. In another aspect, the nucleic acid probe is a polynucleotide that encodes the polypeptide of SEQ ID NO: 2 or a fragment thereof; the mature polypeptide of SEQ ID NO: 3 or a fragment thereof; or the polypeptide of SEQ ID NO: 4 or a fragment thereof. In another aspect, the nucleic acid probe is SEQ ID NO: 1 or the cDNA sequence thereof.

In one aspect, the nucleic acid probe is the mature polypeptide coding sequence of SEQ ID NO: 7. In another aspect, the nucleic acid probe comprises nucleotides 82-683 of SEQ ID NO: 7. In another aspect, the nucleic acid probe is a polynucleotide that encodes the polypeptide of amino acids 28-231 of SEQ ID NO: 8 or a fragment thereof; the mature polypeptide of SEQ ID NO: 3 or a fragment thereof; or the polypeptide of SEQ ID NO: 4 or a fragment thereof. In another aspect, the nucleic acid probe is nucleotides 82-683 of SEQ ID NO: 7 or the cDNA sequence thereof.

In another embodiment, the parent is encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the parent is encoded by a polynucleotide having a sequence identity to nucleotides 82-683 of SEQ ID NO: 7 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent xylanase may be obtained from microorganisms of any genus. For purposes of the present invention, the term "obtained from" as used herein in connection with a given source shall mean that the parent xylanase encoded by a polynucleotide is produced by the source or by a strain in which the polynucleotide from the source has been inserted. In one aspect, the parent xylanase is secreted extracellularly.

The parent may be a bacterial GH Family 11 xylanase. For example, the parent may be a bacterial polypeptide such as a *Bacillus, Cellulomonas, Cellvibrio, Clostridium, Dictyoglomus, Fibrobacter, Geobacillus, Lactococcus, Micromonospora, Norcardiopsis, Paenibacillus, Pseudobutyrivibrio, Ruminococus, Sorangium, Streptococcus, Streptomyces, Thermobacillus, Thermobifida, Thermobispora,* or *Thermopolyspora* GH Family 11 xylanase.

In one aspect, the parent is a *Bacillus amyloliquefaciens, Bacillus cereus, Bacillus circulans, Bacillus lichenformis, Bacillus pumilus, Bacillus subtilis, Cellulomonas fimi, Cellulomonas flavigena, Cellvibrio japonicuus, Clostridium acetobutylicum, Clostridium cellulolyticum, Clostridium cellovorans, Clostridium clariflavum, Clostridium saccharobutylicum, Clostridium thermocellum, Dictyoglomus thermophilum, Fibrobacter succinogenes, Geobacillus stearothermophilus, Lactococcus lactis, Micromonospora aurantiaca, Norcardiopsis dassonvillei, Paenibacillus polymyxa, Pseudobutyrivibrio xylanivorans, Ruminococus albus, Ruminococus flavifaciens, Sorangium cellulosum, Streptomyces coelicolor, Streptomyces lividans, Thermobacillus composti, Thermobifida fusca, Thermobispora bispora,* or *Thermopolyspora flexuosa* GH Family 11 xylanase.

The parent may be a fungal GH Family 11 xylanase. For example, the parent may be a yeast GH Family 11 xylanase such as a *Candida, Kluyveromyces, Pichia, Saccharomyces, Schizosaccharomyces,* or *Yarrowia* GH Family 11 xylanase; or a filamentous fungal GH Family 11 xylanase such as an *Aspergillus, Aureobasidium, Botryotinia, Botrytis, Chaetomium, Chrysosporium, Claviceps, Coprinopsis, Coptotermes, Corynascus, Cryptococcus, Fusarium, Gibberella,*

*Holomastigotoides, Humicola, Hypocrea, Lentinula, Leptosphaeria, Magnaporthe, Myceliophthora, Neocallimastix, Neurospora, Orpinomyces, Paecilomyces, Penicillium, Phanerochaete, Piriformospora, Piromyces, Podospora, Pyrenophora, Rhizomucor, Rhizopus, Schizophyllum, Sclerotinia, Scytalidium, Talaromyces, Thermomyces, Thielavia, Trichoderma,* or *Verticillium,* GH Family 11 xylanase.

In another aspect, the parent is an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Aureobasidium pullulans, Botryotinia fuckeliana, Botrytis cinerea, Chaetomium thermophilum, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Claviceps purpurea, Coprinopsis cinerea, Coptotermes formosanus, Cryptococcus flavis, Fusarium bactridioides, Fusarium fujikuroi, Fusarium graminearum, Fusarium graminum, Fusarium oxysporum, Fusarium venenatum, Humicola grisea, Humicola insolens, Hypocrea jecorina, Hyprocrea orientalis, Magnaporthe grisea, Myceliophthora thermophila, Neocallimastix frontalis, Neocallimastix patriciarum, Neurospora crassa, Orpinomyces* sp., *Penicillium canescens, Penicillium chrysogenum, Penicillium purpurogenum, Phanerochaete chrysosporium, Piriformospora indica, Piromyces communis, Podospora anserina, Pyrenophora teres, Rhizopus oryzae, Schizophyllum commune, Sclerotinia sclerotiorum, Scytalidium acidophilum, Scytalidium thermophilum, Talaromyces cellulolyticus, Talaromyces emersonni, Talaromyces funiculosus, Thermomyces lanuginosus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei, Trichoderma viride,* or *Verticillium dahliae* GH Family 11 xylanase.

In another aspect, the parent xylanase is a *Trichoderma reesei* GH Family 11 xylanase e.g., the polypeptide of SEQ ID NO: 2, the mature polypeptide of SEQ ID NO: 3, the polypeptide of SEQ ID NO: 4, or the polypeptide of amino acids 28-231 of SEQ ID NO: 8.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having xylanase activity, comprising: (a) introducing into a parent xylanase an amino acid substitution at one or more (e.g., several) positions corresponding to positions 120, 17, 24, 46, 49, 69, and 180 of SEQ ID NO: 2, wherein the variant has xylanase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a GH Family 11 xylanase variant of the present invention.

Nucleic Acid Constructs

The present invention also relates to nucleic acid constructs comprising a polynucleotide encoding a GH Family 11 xylanase variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, and *Trichoderma reesei* beta-xylosidase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, *Aspergillus oryzae* glucoamylase promoter, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Hypocrea, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Hypocrea jecorina, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Fungal cells may also be transformed by a biolistic process involving introduction of gold or tungsten pellets coated with one or more polynucleotides into fungal spores using a particle gun. Suitable methods for biolistic transformation of *Trichoderma* host cells are described in U.S. Publication No. 2013/0052694.

Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a variant of the present invention. Preferably, the compositions are enriched in such a variant. The term "enriched" means that the xylanase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, or *Aspergillus oryzae*; *Fusarium*, e.g., *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, e.g., *Humicola insolens* or *Humicola grisea*; *Hypocrea*, e.g., *Hypocrea jecorina*, *Myceliophthora*, e.g., *Myceliophthora thermophila*, *Penicillium*, e.g., *Penicillium funiculosum*, or *Trichoderma*, e.g., *Trichoderma harzianum*, *Trichoderma koningii*, *Trichoderma longibrachiatum*, *Trichoderma reesei*, or *Trichoderma viride*.

The compositions may be prepared in accordance with methods known in the art and may be in the form of a liquid or a dry composition. For instance, the composition may be in the form of a granulate or microgranulate. The variant may be stabilized in accordance with methods known in the art.

The compositions may be a fermentation broth formulation or a cell composition, as described herein. Consequently, the present invention also relates to fermentation broth formulations and cell compositions comprising a polypeptide having xylanase activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as cellobiohydrolase, endoglucanase, beta-glucosidase, endo-beta-1,3 (4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextrinases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the invention. The dosage of the composition of the invention and other conditions under which the composition is used may be determined on the basis of methods known in the art.

Uses

A variant of the present invention may be used in several applications to degrade or convert a xylan-containing material comprising treating the material with the variant (see, for example, WO 02/18561). A variant of the present invention may be used to enhance the brightness of pulp, to improve the quality of paper, to decrease the amount of chemical bleaching agents such as chlorine used in the pulp bleaching stages, and to treat pulp for other purposes, without inducing any damage of cellulose in pulp.

The variants may be used in methods for the treatment of pulp, e.g., Kraft pulp, according to U.S. Pat. No. 5,658,765. Pulp is a dry fibrous material prepared by chemically or mechanically separating fibers from wood, fiber crops, or waste paper. Wood pulp is the most common material used to make paper. The timber resources used to make wood pulp are referred to as pulpwood. Wood pulp comes from softwood trees such as spruce, pine, fir, larch, and hemlock, and hardwoods such as eucalyptus, aspen, and birch. The variants can be used in bleaching of pulp to reduce the use of toxic chlorine-containing chemicals. In addition, it is desirable that xylanases used for biobleaching are stable and active under alkaline conditions at high temperatures. In a preferred embodiment, the present invention relates to methods for treating a pulp, comprising contacting the pulp with the variant.

In the pulp treatment according to the present invention, conditions of the enzymes for treating pulp, such as temperature, pH, pressure, time period, etc., may be suitably chosen so that the desired enzymatic action is exhibited to achieve the desired effects such as enhancement of the brightness. For example, the temperature may be in the range of 10 to 90° C., e.g., 25 to 85° C., 30 to 85° C., 40 to 85° C., 50 to 85° C., 60 to 80° C., 70 to 80° C., or any other suitable temperature. The pH may be in the range of 3 to 11, e.g., 4 to 10, 5 to 10, 6 to 10, 7 to 10, 7 to 9.5, 8 to 9.5, or any other suitable pH. The pulp is treated with a variant in the amount of 0.1 to 25 mg/kg dry pulp, e.g., 0.25 to 20, 0.5 to 10, 0.75 to 10, 1 to 8, 1 to 6, 1 to 5 mg/kg dry pulp, or any other suitable amount.

The pressure may be applied under such a pressure conventionally used for pulp bleaching or other ordinary pulp treating steps; there is no particular restriction but normal pressure is preferably from an economic standpoint. The time period for the treatments may be in the range of 10 minutes to 50 hours, e.g., 0.5 hour to 24 hours, 1 hour to 24 hours, 1 hour to 12 hours, 1 hour to 5 hours, e.g., 2 hours, or any other suitable time period.

In the case where it is desired to enhance the brightness, the amount of a chemical bleaching agent used after the enzymatic treatment can be greatly reduced. The pulp treatment of the present invention is sufficient as a substitute for at least a part of the current bleaching process using chlorine bleaching agents.

The method of the present invention for treating pulp is applicable to a wide range of pulp derived from a broadleaf tree, a needle-leaf tree, or a non-tree material, such as kraft pulp, sulfite pulp, semi-chemical pulp, groundwood pulp, refiner groundwood pulp, thermo-mechanical pulp, etc. By applying the pulp treatment method of the present invention to these pulps, the amount of lignin remaining in the pulp can be reduced to attain the effects such as enhancement of the brightness of pulps, improvement of the quality, and decrease of the amount of a chemical bleaching agent. The pulp treatment method of the present invention may also be applied to the bleaching steps of these pulps by oxygen or the like, prior to or after the bleaching.

Following the pulp treatment using a variant of the present invention, an extraction may also be carried out to effectively remove the lignin dissolved or susceptible to be dissolved out of the pulp. The extraction may be performed using, e.g., sodium hydroxide. In this case, typical conditions for the extraction are set forth to have a pulp concentration of 0.3 to 20%, a sodium hydroxide concentration of 0.5 to 5% based on the weight of dry pulp, a temperature range of 40 to 80° C., and a time period for 30 minutes to 3 hours, e.g., 1 to 2 hours. However, any suitable extraction known in the art may be used.

After the pulp is treated according to the method of the present invention, a chemical bleaching agent may also be used to further enhance the brightness of the pulp. In this case, even if the amount of the chemical bleaching agent is greatly decreased as compared to the case of bleaching pulp only with the chemical bleaching agent, a better brightness can be obtained. Where chlorine dioxide is used as a chemical bleaching agent, the amount of chlorine dioxide can be reduced by 23 to 43% or even more.

When paper is made from the pulp treated according to the method of the present invention, the paper has excellent properties such as a lower content of chlorinated phenol compounds, as compared to paper prepared from conventional bleached pulp.

The variants may also be used in processes for producing xylose or xylo-oligosaccharide according to U.S. Pat. No. 5,658,765. In another preferred embodiment, the present invention relates to methods for producing xylose, comprising contacting a xylan-containing material with the variant. In one aspect, the method further comprises recovering the xylose.

The variants may also be used as feed enhancing enzymes that improve feed digestibility to increase the efficiency of its utilization according to U.S. Pat. No. 6,245,546.

The variants may also be used in baking according to U.S. Pat. No. 5,693,518.

The variants may further be used in brewing according to WO 02/24926.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or amino acid substitutions in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention is further described by the following examples that should not be construed as limiting the scope of the invention.

EXAMPLES

Example 1 describes the strains and vectors used in subsequent examples. Examples 2 and 3 describe generation random mutagenesis libraries parental GH Family 11 xylanases. Example 4 describes construction of GH Family 11 xylanase variants containing multiple amino acid substitutions. Examples 5 and 6 describe the expression of GH Family 11 xylanase variants from microculture and the high-throughput screening to identify modified GH Family 11 xylanase variants with increased thermoactivity and/or thermostability. Example 7 describes methods for determining the temperature profiles of thermoactive GH Family 11 xylanase variants. Example 8 describes the high-throughput screening to identify modified GH Family 11 xylanase variants with lower pH activity profile. Example 9 describes methods for determining the pH profiles of GH Family 11 xylanase variants.

Example 1: Strains and Vectors

*Saccharomyces cerevisiae* strain YNL219C BY4742 [11993] (MATα his3Δ1 leu2Δ0 lys2Δ0 ura3Δ0 Δalg9) was obtained from ATCC (cat. No. 4011993). *Escherichia coli* strain DH5α (F-φ80lacZΔM15 Δ(lacZYA-argF)U169 recA1 endA1 hsdR17(rk−, mk+) phoA supE44 thi-1 gyrA96 relA1λ-) was obtained from Invitrogen (cat. No. 18265-017).

Figure 1:
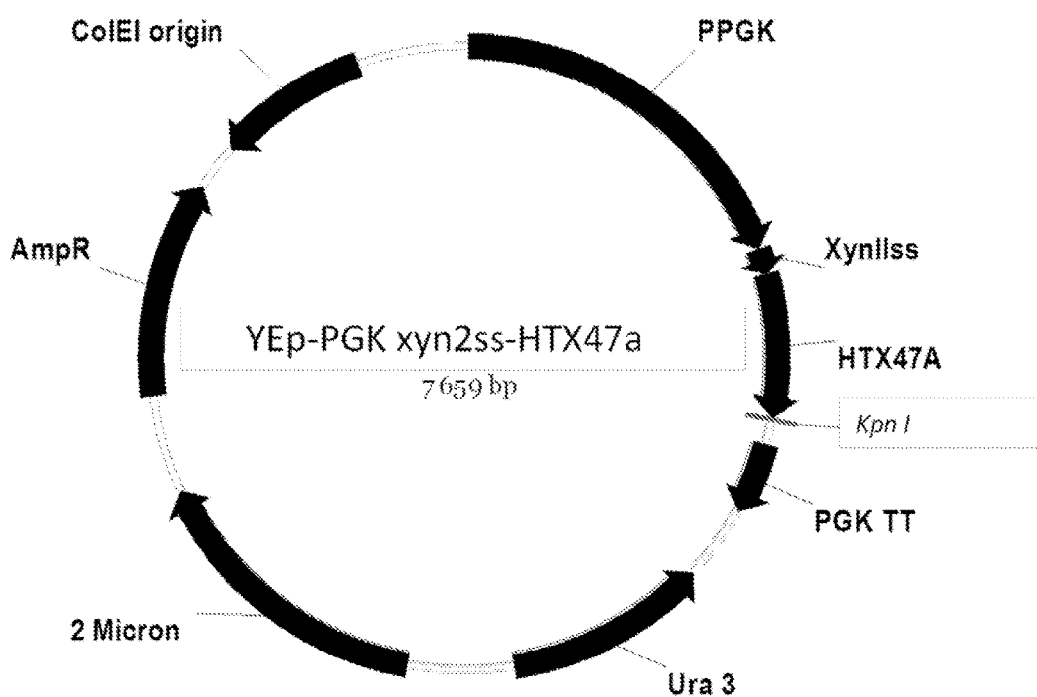
FIG. 1 shows vector map of YEp352/PGKxylss-HTX47A used to express GH11 xylanase variants from *Saccharomyces cerevisiae* and to perform random mutagenesis.

The YEp352/PGKxylss-HTX47a vector was constructed by replacing the *T. reesei* Cel5A sequence in YEp352/PGKxylss-Cel5A, described in U.S. Publication No. 2013/0095554, with a polynucleotide encoding the HTX47A xylanase variant operably linked to the xylanase II secretion signal sequence (XynII ss). A map of vector YEp352/PGKxylss-HTX47a is shown in FIG. 1.

Example 2: Random Mutagenesis of Parental Xylanase HTX47A

HTX47A is a variant of *T. reesei* xylanase II containing the mutations N10H+N11D+Y27M+N29L+S40R+K58R+S75A+S99C+L105H+Y118C+Q125A+I129E+T131N (WO 2007/115407) Four random mutagenesis libraries of the polynucleotide encoding the HTX47A xylanase were constructed as follows: PCR was performed for 20 amplification cycles using 0.2, 2.0 and 20 fmol of YEp352/PGKxylss-HTX47A as template with primers DK510 and PGKterm. This vector fragment and each final amplicon were transformed simultaneously and cloned by in vivo recombination into yeast strain YNL219C BY4742 [11993] (Butler et al., 2003).

```
DK510
                                       (SEQ ID NO: 5)
5' TGG CTG TGG AGA AGC GC

PGK-term
                                       (SEQ ID NO: 6)
5' GCA ACA CCT GGC AAT TCC TTA CC
```

Example 3: Random Mutagenesis of Parental Xylanase HTX47A+H105Y+T120S+Q162H+F180Y ("HTX47A (TS004)")

A random mutagenesis library of the polynucleotide encoding the parental xylanase HTX47A(TS004) was constructed as follows: PCR was performed for 20 amplification cycles using 0.2, 2.0 and 20 fmol of YEp352/PGKxylss-HTX47A as template with primers DK510 and PGKterm. This vector fragment and each final amplicon were transformed simultaneously and cloned by in vivo recombination into yeast strain YNL219C BY4742 [11993] (Butler et al., 2003).

```
DK510
                                        (SEQ ID NO: 5)
5' TGG CTG TGG AGA AGC GC

PGK-term
                                        (SEQ ID NO: 6)
5' GCA ACA CCT GGC AAT TCC TTA CC
```

Example 4: Construction of GH Family 11 Xylanase Variants Containing Multiple Amino Acid Substitutions Polynucleotides encoding GH Family 11 xylanase variants TS003, TS004, and TS005—each containing multiple amino acid substitutions identified in Examples 2 and 3 (listed Table 2, below)—were synthesized de novo by GenScript to include 5'-NheI and 3'-KpnI flanking restriction sites; these were received in the pUC57 vector. The polynucleotides were excised using a NheI/KpnI double digest and ligated into a correspondingly linearized YEp-PGK-xyn2ss-HTX47 vector.

TABLE 2

Mutations in GH Family 11 xylanase variants TS003, TS004, TS005, TS011 and TS012 vs. parent HTX47A xylanase (containing the mutations N10H + Y27M + N29L + S75A + L105H + Q125A + I129E + N11D + S40R + K58R + S99C + Y118C + T131N)

| Variant | Mutations |
| --- | --- |
| TS003 | HTX47A + L105Y + T120S |
| TS004 | HTX47A + L105Y + T120S + Q162H + F180Y |
| TS005 | HTX47A + N10Q + K49E + L105Y + T120S + Q162H + F180Y |
| TS011 | HTX47A + G24C + L105Y + T120S + Q162H + F180Y |
| TS012 | HTX47A + Y17F + G24C + L105Y + T120S + Q162H + F180Y |

Example 5: Expression and Isolation of GH Family 11 Xylansae Variants from Yeast Microplate Cultures This example describes the selection and expression of Family 11 xylanase variants from *Saccharomyces cerevisiae* for use in a high-throughput screening assay.

*Saccharomyces cerevisiae* transformants from the libraries described in Examples 2, 3 and 4 were grown on plates containing synthetic complete medium (SC: 2% agar w/v, 0.17% yeast nitrogen base w/v, 0.078%-Ura drop-out supplement w/v, 2% glucose w/v, 2% casamino acids w/v, 0.5% ammonium sulfate w/v, pH 5.5) and 0.12% Azo-WAX (Megazyme) for 3 days at 30° C.

Colonies showing visible clearing halos were selected for liquid media cultures by toothpick inoculation of 1 mL synthetic complete media (SC: 0.17% yeast nitrogen base w/v, 0.078%-Ura drop-out supplement w/v, 2% glucose w/v, 2% casamino acids w/v, 0.5% ammonium sulfate w/v, pH 5.5) in 96-deepwell microplates. Cultures were grown for 3 days at 30° C. and 250 rpm with humidity control. Glycerol stocks were made combining 100 μL of culture with 100 μL of 30% glycerol and stored at −80° C. Deepwell culture plates were then centrifuged at 3000 rpm for 5 minutes to pellet cells and supernatant was aspirated for screening assays.

Example 6: Screening of *T. reesei* HTX47A Libraries for GH Family 11 Xylanase Variants with Increased Thermoactivity This example describes the screening of HTX47A xylanase variant for improved thermoactivity relative to the parental HTX47A that had been cloned into *Saccharomyces cerevisiae*.

An aliquot of supernatant (50 μL) from each parental and variant microculture, produced as in Example 5, was added to 50 μL of 1.0% wheat arabinoxylan (Megazyme; medium viscosity) buffered with 50 mM citrate phosphate at pH 5.0 and incubated at 65° C. for 1 hour. An identical assay was performed at 79° C. Microculture supernatants for the 65° C. assay were diluted 1 in 5 while supernatants for the 79° C. assay were diluted 1 in 2. Both assays were performed in a PCR plate and incubations were performed in a Tetrad thermalcycler. Contained in each 96-well PCR plate were six parental HTX47A controls used for comparison. Assays were done in duplicate. Following each incubation, 80 μL of dinitrosalicyclic acid was added and the plates were heated to 95° C. for 5 min. A 135 μL aliquot of the solution was transferred to a microplate and the absorbance at 560 nm was measured.

Figure 2:
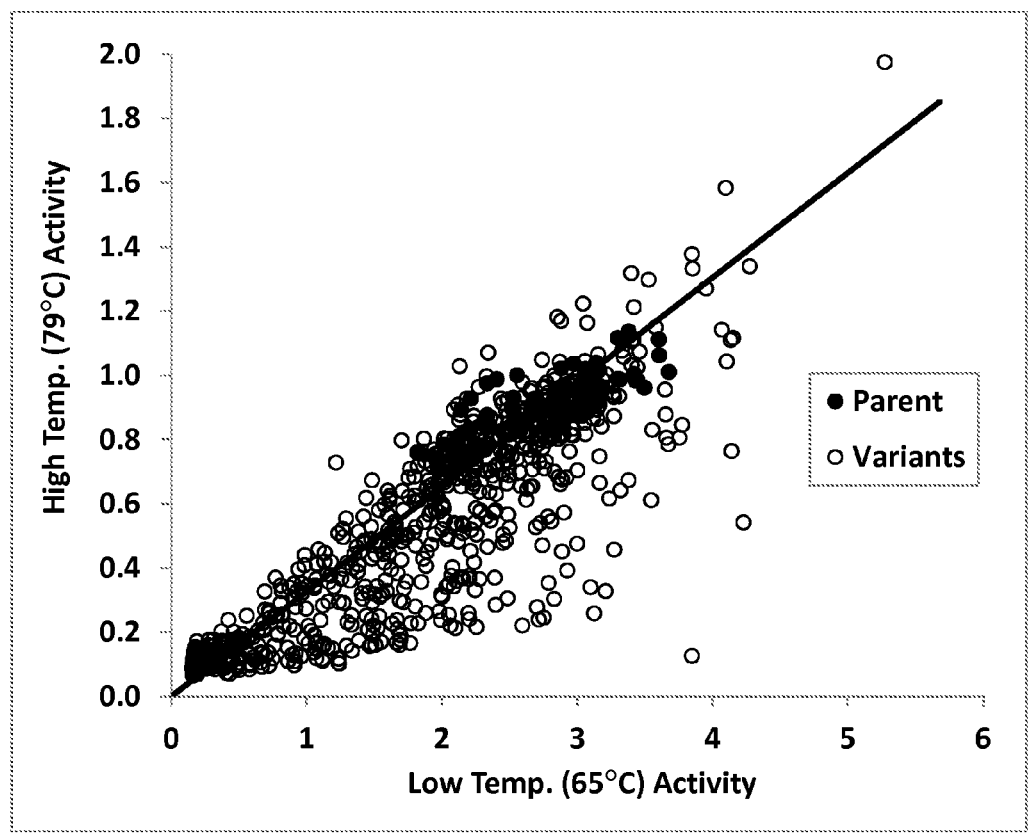
FIG. 2 shows thermoactivity data from one full round of screening. Plotted on the y-axis is xylanase activity at the high temperature (79° C.) and plotted on the x-axis is xylanase activity at the low temperature (65° C.) for GH11 xylanase variants and parental xylanase controls.
Figure 3:
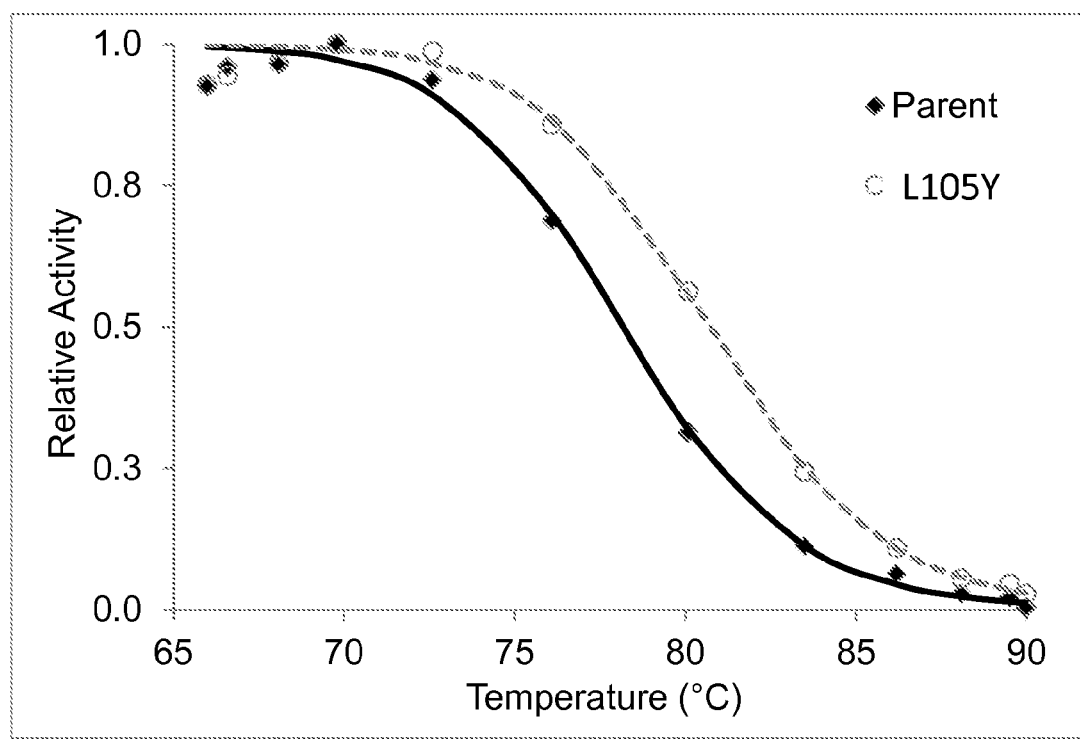
FIG. 3 shows the thermoactivity profiles for a parental GH11 xylanase (TrXyn2+N10D+N11D+Y27M+N29L+S40R+K58R+S75A+S99C+L105H+Y118C+Q125A+I129E+T131N) and a GH11 xylanase variant (TrXyn2+N10D+N11D+Y27M+N29L+S40R+K58R+S75A+S99C+L105Y+Y118C+Q125A+I129E+T131N). Relative activity was calculated by dividing the activity at each temperature by the maximal activity.
Figure 4:
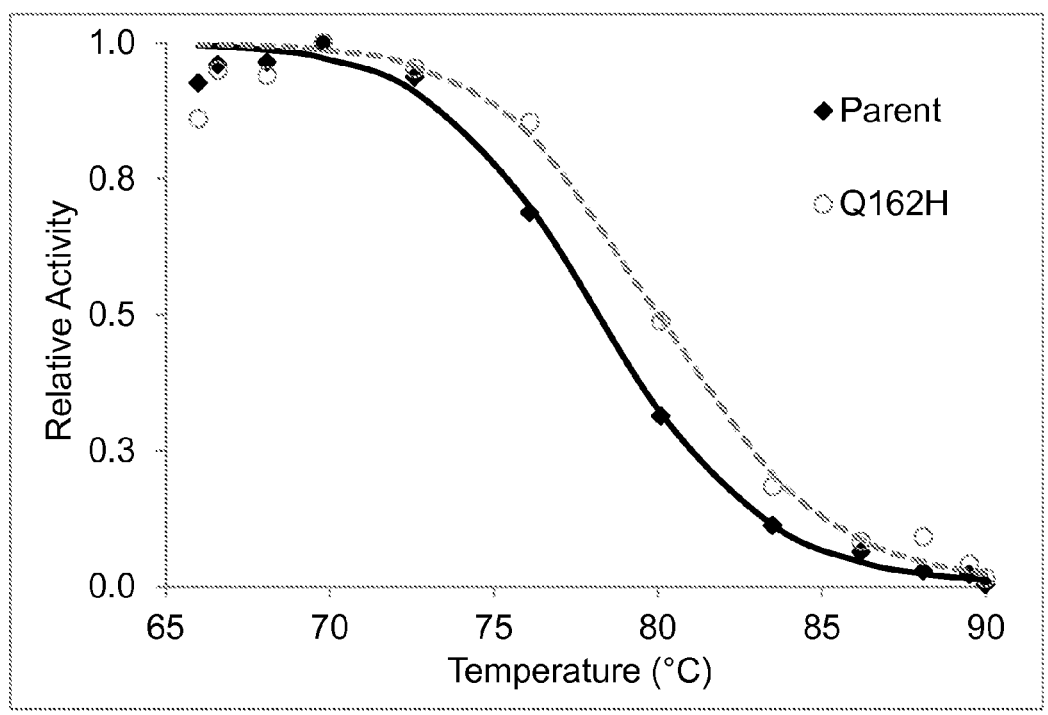
FIG. 4 shows the thermoactivity profiles for a parental GH11 xylanase (TrXyn2+N10D+N11D+Y27M+N29L+S40R+K58R+S75A+S99C+L105H+Y118C+Q125A+I129E+T131N) and a GH11 xylanase variant (TrXyn2+N10D+N11D+Y27M+N29L+S40R+K58R+S75A+S99C+L105H+Y118C+Q125A+I129E+T131N+Q162H). Relative activity was calculated by dividing the activity at each temperature by the maximal activity.
Figure 5:
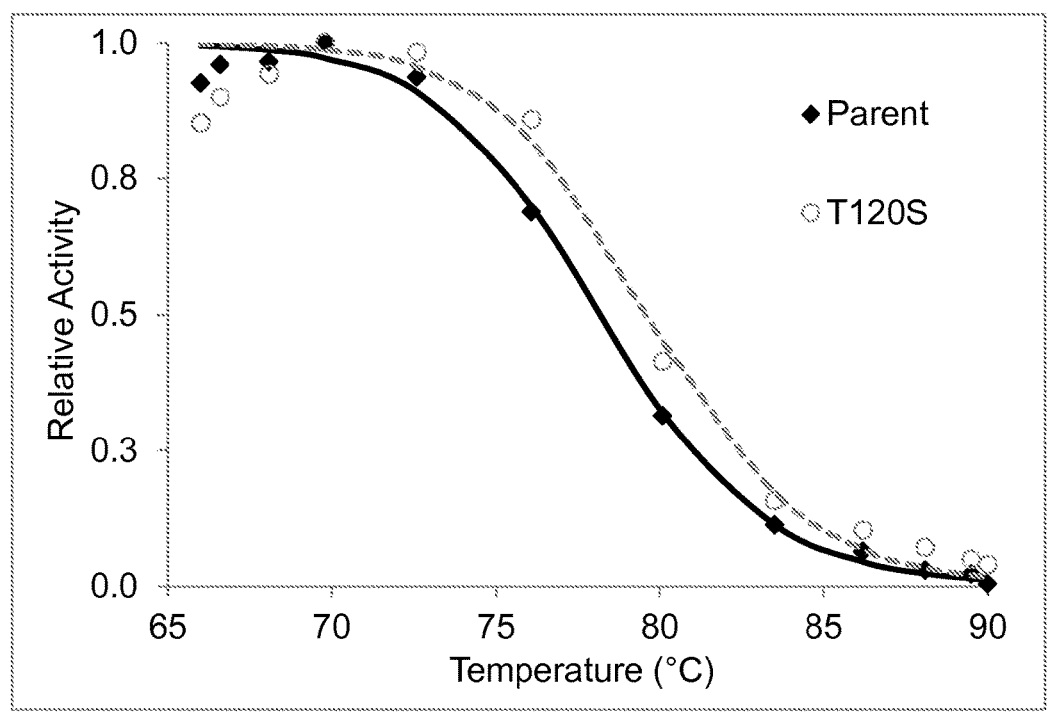
FIG. 5 shows the thermoactivity profiles for a parental GH11 xylanase (TrXyn2+N10D+N11D+Y27M+N29L+S40R+K58R+S75A+S99C+L105H+Y118C+Q125A+I129E+T131N) and a GH11 xylanase variant (TrXyn2+N10D+N11D+Y27M+N29L+S40R+K58R+S75A+S99C+L105H+Y118C+T120S+Q125A+I129E+T131N). Relative activity was calculated by dividing the activity at each temperature by the maximal activity.
Figure 6:
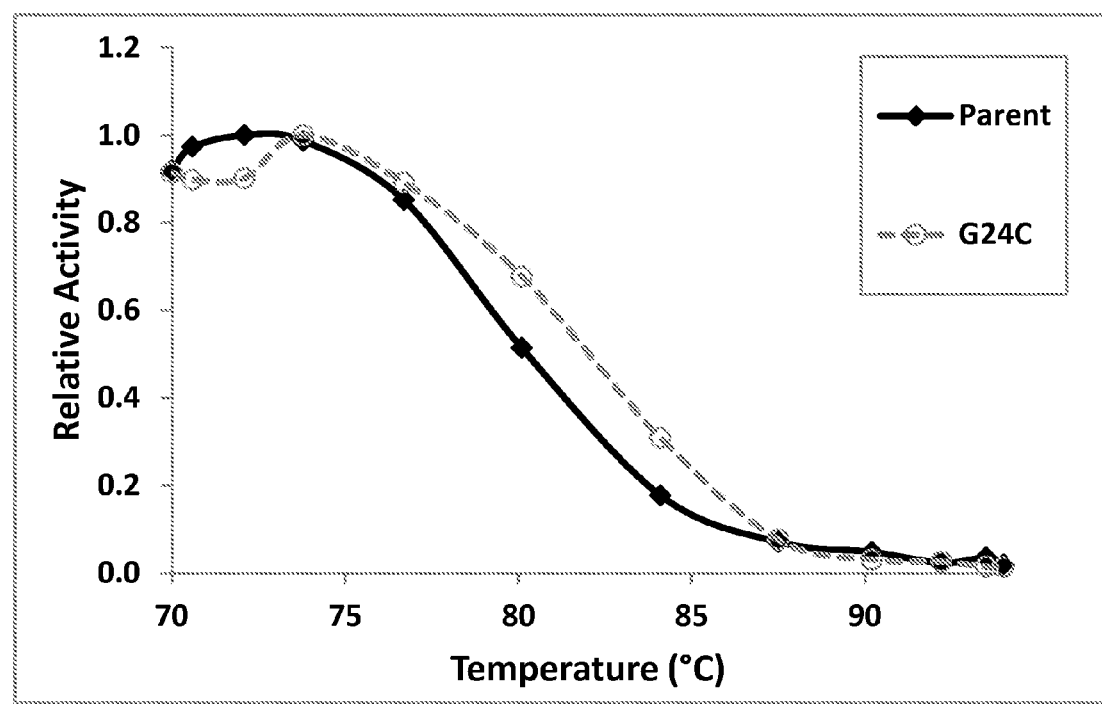
FIG. 6 shows the thermoactivity profiles for a parental GH11 xylanase (TrXyn2+N10D+N11D+Y27M+N29L+S40R+K58R+S75A+S99C+L105H+Y118C+T120S+Q125A+I129E+T131N+Q162H+F180Y) and a GH11 xylanase variant (TrXyn2+N10D+N11D+G24C+Y27M+N29L+S40R+K58R+S75A+S99C+L105H+Y118C+

The absorbance for data relating to the plate incubated at 65° C. and 79° C. was multiplied by 5 and 2, respectively (supernatant dilution factor) for all variants and parental controls. A high/low temperature activity ratio was then calculated by dividing the corrected absorbance at 65° C. by the corrected absorbance at 79° C. for each of the six parental controls and an average and standard deviation was calculated. A high/low temperature activity ratio was also calculated for each TrXyn2 variant. Positives were then selected greater than 2 standard deviations above the average parental control. All positive modified TrXyn2s were re-screened to reduce the number of false positives. Screening data from one complete round of screening can be found in FIG. 2.

Example 7: Determining the Temperature Profile for Selected HTX47A Xylanase Variants An aliquot of supernatant (50 μL; diluted 5-fold) from selected microcultures was added to 50 μL of 1.0% wheat arabinoxylan (Megazyme; medium viscosity) buffered with 50 mM sodium citrate at pH 5.0 and incubated at various temperatures for 1 hour. These assays were performed in a PCR plate and incubations were performed in a Tetrad thermalcycler. Assays were done in duplicate. Following each incubation 80 μL of dinitrosalicyclic acid was added and the plates were heated to 95° C. for 5 min. A 135 μL aliquot of the solution was transferred to a microplate and the absorbance at 560 nm was measured. Temperature profiles for selected TrXyn2 variants and parental controls can be found in FIGS. 3-8.

Example 8: Screening of *Trichoderma reesei* Xyn2 Library for Modified Family 11 Xylanases with Increased Activity at Lower pH This example describes the screening of modified *Trichoderma reesei* Xyn2 xylanases for improved activity at lower pH relative to the parental TrXyn2 that had been cloned into *Saccharomyces cerevisiae*.

An aliquot of supernatant (50 µL) from each parental and variant microculture was added to 50 µL of 1.0% wheat arabinoxylan (Megazyme; medium viscosity) buffered with 50 mM sodium citrate at pH 5 and incubated at 65° C. for 1 hour. An identical assay was performed at pH 3. Microculture supernatants for the pH 5 assay were diluted 1 in 5 while supernatants for the pH 3 assay were diluted 1 in 3. Both assays were performed in a PCR plate and incubations were performed in a Tetrad thermalcycler. Contained in each 96-well PCR plate were six parental TrXyn2 controls used for comparison. Assays were done in duplicate. Following each incubation, 80 µL of dinitrosalicyclic acid was added and the plates were heated to 95° C. for 5 min. A 135 µL aliquot of the solution was transferred to a microplate and the absorbance at 560 nm was measured.

The absorbance for data relating to the plate incubated at pH 5 and pH 3 was multiplied by 5 and 3, respectively (supernatant dilution factor) for all variants and parental controls. A low/high pH activity ratio was then calculated by dividing the corrected absorbance at pH 3 by the corrected absorbance at pH 5 for each of the six parental controls and an average and standard deviation was calculated. A low/high pH activity ratio was also calculated for each TrXyn2 variant. Positives were then selected greater than 2 standard deviations above the average parental control. All positive modified TrXyn2s were re-screened to reduce the number of false positives. Screening data from one complete round of screening can be found in FIG. 9.

Example 9: Determining the pH Profile for Selected GH Family 11 Xylanase Variants An aliquot of supernatant (50 µL; diluted 5-fold) from selected microcultures was added to 50 µL of 1.0% wheat arabinoxylan (Megazyme; medium viscosity) buffered with 50 mM citrate/phosphate at various pHs and incubated at 65° C. for 1 hour. These assays were performed in a PCR plate and incubations were performed in a Tetrad thermalcycler. Assays were done in duplicate. Following each incubation 80 µL of dinitrosalicyclic acid was added and the plates were heated to 95° C. for 5 min. A 135 µL aliquot of the solution was transferred to a microplate and the absorbance at 560 nm was measured.

The invention is further defined by the following paragraphs:

Paragraph 1. A variant of GH Family 11 xylanase, comprising a substitution at one or more (e.g., several) positions corresponding to positions 120, 17, 24, 46, 49, 69, and 180 of the polypeptide of SEQ ID NO: 2 or SEQ ID NO: 4, wherein the variant has xylanase activity.

Paragraph 2. A variant of GH Family 11 xylanase, comprising a substitution at one or more (e.g., several) positions corresponding to positions 120, 17, 24, 46, 49, 69, and 180 of the polypeptide of SEQ ID NO: 2 or SEQ ID NO: 4, wherein the variant has xylanase activity and wherein the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent xylanase.

Paragraph 3. A variant of GH Family 11 xylanase, comprising a substitution at one or more (e.g., several) positions corresponding to positions 120, 17, 24, 46, 49, 69, and 180 of the polypeptide of SEQ ID NO: 2 or SEQ ID NO: 4, wherein the variant has xylanase activity and wherein the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent xylanase of SEQ ID NO:2, amino acids 34-223 of SEQ ID NO: 3, or SEQ ID NO: 4.

Paragraph 4. The variant of any of paragraphs 1 to 3, which is a variant of a parent GH Family 11 xylanase selected from the group consisting of:

a. a polypeptide having at least 60% sequence identity to SEQ ID NO: 2, SEQ ID NO: 4, or amino acids 28-231 of SEQ ID NO: 8;

b. a polypeptide encoded by a polynucleotide that hybridizes under at least low stringency conditions with (i) the mature polypeptide coding sequence of SEQ ID NO: 1 or SEQ ID No: 7, (ii) the cDNA sequence thereof, or (iii) the full-length complement of (i) or (ii);

c. a polypeptide encoded by a polynucleotide having at least 60%, identity to the mature polypeptide coding sequence of SEQ ID NO: 1 or SEQ ID No: 7, or the cDNA sequence thereof; and d. a fragment of SEQ ID NO: 2, SEQ ID NO: 4, or amino acids 28-231 of SEQ ID NO: 8, which has xylanase activity.

Paragraph 5. The variant of any of paragraphs 2 to 4 wherein the parent GH Family 11 xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO:2, amino acids 34-223 of SEQ ID NO: 3, SEQ ID NO: 4, or amino acids 28-231 of SEQ ID NO: 8.

Paragraph 6. The variant of any of paragraphs 2 to 5 wherein the parent GH Family 11 xylanase is a polypeptide encoded by a polynucleotide that hybridizes under at least low stringency conditions with (i) the mature polypeptide coding sequence of SEQ ID NO: 1 or SEQ ID No: 7, (ii) the cDNA sequence thereof, or (iii) the full-length complement of (i) or (ii).

Paragraph 7. The variant of any of paragraphs 2 to 5 wherein the parent GH Family 11 xylanase is a polypeptide encoded by a polynucleotide that hybridizes under at least medium stringency conditions with (i) the mature polypeptide coding sequence of SEQ ID NO: 1 or SEQ ID No: 7, (ii) the cDNA sequence thereof, or (iii) the full-length complement of (i) or (ii).

Paragraph 8. The variant of any of paragraphs 2 to 5 wherein the parent GH Family 11 xylanase is a polypeptide encoded by a polynucleotide that hybridizes under at least high stringency conditions with (i) the mature polypeptide coding sequence of SEQ ID NO: 1 or SEQ ID No: 7, (ii) the cDNA sequence thereof, or (iii) the full-length complement of (i) or (ii).

Paragraph 9. The variant of any of paragraphs 2 to 5 wherein the parent GH Family 11 xylanase is a polypeptide encoded by a polynucleotide that hybridizes under at least very high stringency conditions with (i) the mature polypeptide coding sequence of SEQ ID NO: 1 or SEQ ID No: 7, (ii) the cDNA sequence thereof, or (iii) the full-length complement of (i) or (ii).

Paragraph 10. The variant of any of paragraphs 2 to 5 wherein the parent GH Family 11 xylanase is a polypeptide encoded by a polynucleotide having at least 60%, e.g., at least 65%, at least 70%, at least 75%, at least 80%, at least 85%, at least 90%, at least 95%, at least 96%, at least 97%, at least 98%, at least 99% or 100%, identity to the mature polypeptide coding sequence of SEQ ID NO: 1 or SEQ ID No: 7 or the cDNA sequence thereof.

Paragraph 11. The variant of any of paragraphs 2 to 5 wherein the parent GH Family 11 xylanase is a fragment of SEQ ID NO: 2, SEQ ID NO: 4, or amino acids 28-231 of SEQ ID NO: 8 having xylanase activity.

Paragraph 12. The variant of paragraph 11, wherein the fragment of SEQ ID NO: 2, SEQ ID NO: 4, or amino acids 28-231 of SEQ ID NO: 8 comprises or consists of at least 170 amino acid residues.

Paragraph 13. The variant of paragraph 11, wherein the fragment of SEQ ID NO: 2, SEQ ID NO: 4, or amino acids 28-231 of SEQ ID NO: 8 comprises or consists of at least 180 amino acid residues.

Paragraph 14. The variant of paragraph 11, wherein the fragment of SEQ ID NO: 2, SEQ ID NO: 4, or amino acids 28-231 of SEQ ID NO: 8 comprises or consists of at least 185 amino acid residues.

Paragraph 15. The variant of paragraph 11, wherein the fragment of SEQ ID NO: 2 or SEQ ID NO: 4 comprises or consists of amino acids 1 to 185 of SEQ ID NO: 2 or SEQ ID NO: 4.

Paragraph 16. The variant of paragraph 11, wherein the fragment of SEQ ID NO: 2 or SEQ ID NO: 4 comprises or consists of amino acids 5 to 190 of SEQ ID NO: 2 or SEQ ID NO: 4.

Paragraph 17. The variant of paragraph 11, wherein the fragment of SEQ ID NO: 2 or SEQ ID NO: 4 comprises or consists of, amino acids 10 to 190 of SEQ ID NO: 2 or SEQ ID NO: 4.

Paragraph 18. The variant of paragraph 11, wherein the fragment of SEQ ID NO: 2 or SEQ ID NO: 4 comprises or consists of, amino acids 5 to 185 of SEQ ID NO: 2 or SEQ ID NO: 4.

Paragraph 19. The variant of paragraph 11, wherein the fragment of SEQ ID NO: 2 or SEQ ID NO: 4 comprises or consists of, amino acids 10 to 180 of SEQ ID NO: 2 or SEQ ID NO: 4.

Paragraph 20. The variant of paragraph 11, wherein the fragment of SEQ ID NO: 2 or SEQ ID NO: 4 comprises or consists of, amino acids 1 to 170 of SEQ ID NO: 2 or SEQ ID NO: 4.

Paragraph 21. The variant of any of paragraphs 1 to 20, wherein the number of amino acid substitutions is 1-20, e.g., 1-10 and 1-5, such as 1, 2, 3, 4, 5, 6, 7, 8, 9, 10, 11, 12, 13, 14, 15, 16, 17, 18, 19, or 20, amino acid substitutions.

Paragraph 22. The variant of any of paragraphs 1 to 21, comprising an amino acid substitution at two positions corresponding to any of positions 120, 17, 24, 46, 49, 69, and 180 of the polypeptide of SEQ ID NO: 2 or SEQ ID NO: 4.

Paragraph 23. The variant of any of paragraphs 1 to 21, comprising an amino acid substitution at three positions corresponding to any of positions 120, 17, 24, 46, 49, 69, and 180 of the polypeptide of SEQ ID NO: 2 or SEQ ID NO: 4.

Paragraph 24. The variant of any of paragraphs 1 to 21, comprising an amino acid substitution at four positions corresponding to any of positions 120, 17, 24, 46, 49, 69, and 180 of the polypeptide of SEQ ID NO: 2 or SEQ ID NO: 4.

Paragraph 25. The variant of any of paragraphs 1 to 21, comprising an amino acid substitution at five positions corresponding to any of positions 120, 17, 24, 46, 49, 69, and 180 of the polypeptide of SEQ ID NO: 2 or SEQ ID NO: 4.

Paragraph 26. The variant of any of paragraphs 1 to 21, comprising an amino acid substitution at six positions corresponding to any of positions 120, 17, 24, 46, 49, 69, and 180 of the polypeptide of SEQ ID NO: 2 or SEQ ID NO: 4.

Paragraph 27. The variant of any of paragraphs 1 to 21, comprising an amino acid substitution at each position corresponding to positions 120, 17, 24, 46, 49, 69, and 180 of the polypeptide of SEQ ID NO: 2 or SEQ ID NO: 4.

Paragraph 28. The variant of any of paragraphs 1 to 21, wherein the amino acid at a position corresponding to position 120 of SEQ ID NO: 2 or SEQ ID NO: 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser.

Paragraph 29. The variant of any of paragraphs 1 to 21, which comprises or consists of the substitution T120S of the polypeptide of SEQ ID NO: 2 or SEQ ID NO: 4.

Paragraph 30. The variant of any of paragraphs 1 to 21, wherein the amino acid at a position corresponding to position 17 of SEQ ID NO: 2 or SEQ ID NO: 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe.

Paragraph 31. The variant of any of paragraphs 1 to 21, which comprises or consists of the substitution Y17F of the polypeptide of SEQ ID NO: 2 or SEQ ID NO: 4.

Paragraph 32. The variant of any of paragraphs 1 to 21, wherein the amino acid at a position corresponding to position 24 of SEQ ID NO: 2 or SEQ ID NO: 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys.

Paragraph 33. The variant of any of paragraphs 1 to 21, which comprises or consists of the substitution G24C of the polypeptide of SEQ ID NO: 2 or SEQ ID NO: 4.

Paragraph 34. The variant of any of paragraphs 1 to 21, wherein the amino acid at a position corresponding to position 46 of SEQ ID NO: 2 or SEQ ID NO: 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile.

Paragraph 35. The variant of any of paragraphs 1 to 21, which comprises or consists of the substitution V46I of the polypeptide of SEQ ID NO: 2 or SEQ ID NO: 4.

Paragraph 36. The variant of any of paragraphs 1 to 21, wherein the amino acid at a position corresponding to position 49 of SEQ ID NO: 2 or SEQ ID NO: 4 is substituted with Ala, Arg, Asn, Asp, Cys, Gin, Glu, Gly, His, Ile, Leu, Lys, Met, Phe, Pro, Ser, Thr, Trp, Tyr, or Val, preferably with Met or Glu.

Paragraph 37. The variant of any of paragraphs 1 to 21, which comprises or consists of the substitution K49E or K49M of the polypeptide of SEQ ID NO: 2 or SEQ ID NO: 4.

Paragraph 38. The variant of any of paragraphs 1 to 21, wherein the amino acid at a position corresponding to position 69 of SEQ ID NO: 2 or SEQ ID NO: 4 is substituted with Ala, Arg, Asn, Asp, Cys, Gin, Glu, Gly, His, Ile, Leu, Lys, Met, Phe, Pro, Ser, Thr, Trp, Tyr, or Val, preferably with Asp.

Paragraph 39. The variant of any of paragraphs 1 to 21, which comprises or consists of the substitution N69D of the polypeptide of SEQ ID NO: 2 or SEQ ID NO: 4.

Paragraph 40. The variant of any of paragraphs 1 to 21, wherein the amino acid at a position corresponding to position 180 of SEQ ID NO: 2 or SEQ ID NO: 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr.

Paragraph 41. The variant of any of paragraphs 1 to 21, which comprises or consists of the substitution F180Y of the polypeptide of SEQ ID NO: 2 or SEQ ID NO: 4.

Paragraph 42. The variant of paragraph 22, wherein the two positions are selected from the group consisting of: 120, and 17; 120, and 24; 120, and 46; 120, and 49; 120, and 69; 120, and 180; 17, and 24; 17, and 46; 17, and 49; 17, and 69; 17, and 180; 24, and 46; 24, and 49; 24, and 69; 24, and 180; 46, and 49; 46, and 69; 46, and 180; 49, and 69; 49, and 180; 69, and 180.

Paragraph 43. The variant of paragraph 23, wherein the three positions are selected from the group consisting of: 120, 17, and 24; 120, 17, and 46; 120, 17, and 49; 120, 17, and 69; 120, 17, and 180; 120, 24, and 46; 120, 24, and 49; 120, 24, and 69; 120, 24, and 180; 120, 46, and 49; 120, 46, and 69; 120, 46, and 180; 120, 49, and 69; 120, 49, and 180; 120, 69, and 180; 17, 24, and 46; 17, 24, and 49; 17, 24, and 69; 17, 24, and 180; 17, 46, and 49; 17, 46, and 69; 17, 46, and 180; 17, 49, and 69; 17, 49, and 180; 17, 69, and 180; 24, 46, and 49; 24, 46, and 69; 24, 46, and 180; 24, 49, and 69; 24, 49, and 180; 24, 69, and 180; 46, 49, and 69; 46, 49, and 180; 46, 69, and 180; 49, 69, and 180.

Paragraph 44. The variant of paragraph 24, wherein the four positions are selected from the group consisting of: 120, 17, 24, and 46; 120, 17, 24, and 49; 120, 17, 24, and 69; 120, 17, 24, and 180; 120, 17, 46, and 49; 120, 17, 46, and 69; 120, 17, 46, and 180; 120, 17, 49, and 69; 120, 17, 49, and 180; 120, 17, 69, and 180; 120, 24, 46, and 49; 120, 24, 46, and 69; 120, 24, 46, and 180; 120, 24, 49, and 69; 120, 24, 49, and 180; 120, 24, 69, and 180; 120, 46, 49, and 69; 120, 46, 49, and 180; 120, 46, 69, and 180; 120, 49, 69, and 180; 17, 24, 46, and 49; 17, 24, 46, and 69; 17, 24, 46, and 180; 17, 24, 49, and 69; 17, 24, 49, and 180; 17, 24, 69, and 180; 17, 46, 49, and 69; 17, 46, 49, and 180; 17, 46, 69, and 180; 17, 49, 69, and 180; 24, 46, 49, and 69; 24, 46, 49, and 180; 24, 46, 69, and 180; 24, 49, 69, and 180; 46, 49, 69, and 180.

Paragraph 45. The variant of paragraph 25, wherein the five positions are selected from the group consisting of: 120, 17, 24, 46, and 49; 120, 17, 24, 46, and 69; 120, 17, 24, 46, and 180; 120, 17, 24, 49, and 69; 120, 17, 24, 49, and 180; 120, 17, 24, 69, and 180; 120, 17, 46, 49, and 69; 120, 17, 46, 49, and 180; 120, 17, 46, 69, and 180; 120, 17, 49, 69, and 180; 120, 24, 46, 49, and 69; 120, 24, 46, 49, and 180; 120, 24, 46, 69, and 180; 120, 24, 49, 69, and 180; 120, 46, 49, 69, and 180; 17, 24, 46, 49, and 69; 17, 24, 46, 49, and 180; 17, 24, 46, 69, and 180; 17, 24, 49, 69, and 180; 17, 46, 49, 69, and 180; 24, 46, 49, 69, and 180.

Paragraph 46. The variant of paragraph 26, wherein the six positions are selected from the group consisting of: 120, 17, 24, 46, 49, and 69; 120, 17, 24, 46, 49, and 180; 120, 17, 24, 46, 69, and 180; 120, 17, 24, 49, 69, and 180; 120, 17, 46, 49, 69, and 180; 120, 24, 46, 49, 69, and 180; 17, 24, 46, 49, 69, and 180.

Paragraph 47. The variant of any of paragraphs 1 to 21, which comprises one or more substitutions selected from the group consisting of T120S, Y17F, G24C, V46I, K49M, K49E, N69D, and F180Y.

Paragraph 48. The variant of any of paragraphs 1 to 21, which comprises two or more substitutions selected from the group consisting of T120S, Y17F, G24C, V46I, K49M, K49E, N69D, and F180Y.

Paragraph 49. The variant of paragraph 49, wherein the two substitutions are selected from the group consisting of: T120S, and Y17F; T120S, and G24C; T120S, and V46I; T120S, and K49M or K49E; T120S, and N69D; T120S, and F180Y; Y17F, and G24C; Y17F, and V46I; Y17F, and K49M or K49E; Y17F, and N69D; Y17F, and F180Y; G24C, and V46I; G24C, and K49M or K49E; G24C, and N69D; G24C, and F180Y; V46I, and K49M or K49E; V46I, and N69D; V46I, and F180Y; K49M or K49E, and N69D; K49M or K49E, and F180Y; N69D, and F180Y.

Paragraph 50. The variant of any of paragraphs 1 to 21, which comprises three or more substitutions selected from the group consisting of T120S, Y17F, G24C, V46I, K49M, K49E, N69D, and F180Y.

Paragraph 51. The variant of paragraph 51, wherein the three substitutions are selected from the group consisting of: T120S, Y17F, and G24C; T120S, Y17F, and V46I; T120S, Y17F, and K49M or K49E; T120S, Y17F, and N69D; T120S, Y17F, and F180Y; T120S, G24C, and V46I; T120S, G24C, and K49M or K49E; T120S, G24C, and N69D; T120S, G24C, and F180Y; T120S, V46I, and K49M or K49E; T120S, V46I, and N69D; T120S, V46I, and F180Y; T120S, K49M or K49E, and N69D; T120S, K49M or K49E, and F180Y; T120S, N69D, and F180Y; Y17F, G24C, and V46I; Y17F, G24C, and K49M or K49E; Y17F, G24C, and N69D; Y17F, G24C, and F180Y; Y17F, V46I, and K49M or K49E; Y17F, V46I, and N69D; Y17F, V46I, and F180Y; Y17F, K49M or K49E, and N69D; Y17F, K49M or K49E, and F180Y; Y17F, N69D, and F180Y; G24C, V46I, and K49M or K49E; G24C, V46I, and N69D; G24C, V46I, and F180Y; G24C, K49M or K49E, and N69D; G24C, K49M or K49E, and F180Y; G24C, N69D, and F180Y; V46I, K49M or K49E, and N69D; V46I, K49M or K49E, and F180Y; V46I, N69D, and F180Y; K49M or K49E, N69D, and F180Y.

Paragraph 52. The variant of any of paragraphs 1 to 21, which comprises four or more substitutions selected from the group consisting of T120S, Y17F, G24C, V46I, K49M, K49E, N69D, and F180Y.

Paragraph 53. The variant of paragraph 53, wherein the four substitutions are selected from the group consisting of: T120S, Y17F, G24C, and V46I; T120S, Y17F, G24C, and K49M or K49E; T120S, Y17F, G24C, and N69D; T120S, Y17F, G24C, and F180Y; T120S, Y17F, V46I, and K49M or K49E; T120S, Y17F, V46I, and N69D; T120S, Y17F, V46I, and F180Y; T120S, Y17F, K49M or K49E, and N69D; T120S, Y17F, K49M or K49E, and F180Y; T120S, Y17F, N69D, and F180Y; T120S, G24C, V46I, and K49M or K49E; T120S, G24C, V46I, and N69D; T120S, G24C, V46I, and F180Y; T120S, G24C, K49M or K49E, and N69D; T120S, G24C, K49M or K49E, and F180Y; T120S, G24C, N69D, and F180Y; T120S, V46I, K49M or K49E, and N69D; T120S, V46I, K49M or K49E, and F180Y; T120S, V46I, N69D, and F180Y; T120S, K49M or K49E, N69D, and F180Y; Y17F, G24C, V46I, and K49M or K49E; Y17F, G24C, V46I, and N69D; Y17F, G24C, V46I, and F180Y; Y17F, G24C, K49M or K49E, and N69D; Y17F, G24C, K49M or K49E, and F180Y; Y17F, G24C, N69D, and F180Y; Y17F, V46I, K49M or K49E, and N69D; Y17F, V46I, K49M or K49E, and F180Y; Y17F, V46I, N69D, and F180Y; Y17F, K49M or K49E, N69D, and F180Y; G24C, V46I, K49M or K49E, and N69D; G24C, V46I, K49M or K49E, and F180Y; G24C, V46I, N69D, and F180Y; G24C, K49M or K49E, N69D, and F180Y; V46I, K49M or K49E, N69D, and F180Y.

Paragraph 54. The variant of any of paragraphs 1 to 21, which comprises five or more substitutions selected from the group consisting of T120S, Y17F, G24C, V46I, K49M, K49E, N69D, and F180Y.

Paragraph 55. The variant of paragraph 55, wherein the five substitutions are selected from the group consisting of: T120S, Y17F, G24C, V46I, and K49M or K49E; T120S, Y17F, G24C, V46I, and N69D; T120S, Y17F, G24C, V46I, and F180Y; T120S, Y17F, G24C, K49M or K49E, and N69D; T120S, Y17F, G24C, K49M or K49E, and F180Y; T120S, Y17F, G24C, N69D, and F180Y; T120S, Y17F, V46I, K49M or K49E, and N69D; T120S, Y17F, V46I, K49M or K49E, and F180Y; T120S, Y17F, V46I, N69D, and F180Y; T120S, Y17F, K49M or K49E, N69D, and F180Y; T120S, G24C, V46I, K49M or K49E, and N69D; T120S, G24C, V46I, K49M or K49E, and F180Y; T120S, G24C, V46I, N69D, and F180Y; T120S, G24C, K49M or K49E, N69D, and F180Y; T120S, V46I, K49M or K49E, N69D, and F180Y; Y17F, G24C, V46I, K49M or K49E, and N69D; Y17F, G24C, V46I, K49M or K49E, and F180Y; Y17F, G24C, V46I, N69D, and F180Y; Y17F, G24C, K49M or K49E, N69D, and F180Y; Y17F, V46I, K49M or K49E, N69D, and F180Y; G24C, V46I, K49M or K49E, N69D, and F180Y.

Paragraph 56. The variant of any of paragraphs 1 to 21, which comprises six or more substitutions selected from the group consisting of T120S, Y17F, G24C, V46I, K49M, K49E, N69D, and F180Y.

Paragraph 57. The variant of paragraph 57, wherein the six substitutions are selected from the group consisting of: T120S, Y17F, G24C, V46I, K49M or K49E, and N69D; T120S, Y17F, G24C, V46I, K49M or K49E, and F180Y; T120S, Y17F, G24C, V46I, N69D, and F180Y; T120S, Y17F, G24C, K49M or K49E, N69D, and F180Y; T120S, Y17F, V46I, K49M or K49E, N69D, and F180Y; T120S, G24C, V46I, K49M or K49E, N69D, and F180Y; Y17F, G24C, V46I, K49M or K49E, N69D, and F180Y.

Paragraph 58. The variant of any of paragraphs 1 to 21, which comprises amino acid substitutions T120S, Y17F, G24C, V46I, K49M, K49E, N69D, and F180Y.

Paragraph 59. The variant of any of paragraphs 1 to 21, further comprising an amino acid substitution at a position corresponding to position 10 of SEQ ID NO: 2.

Paragraph 60. The variant of paragraph 58, wherein the amino acid at substitution at a position corresponding to position 10 is substituted with Ala, Arg, Asp, Cys, Gln, Glu, Gly, His, Ile, Leu, Lys, Met, Phe, Pro, Ser, Thr, Trp, Tyr, or Val, preferably with Gin, Tyr, or Arg.

Paragraph 61. The variant of any of paragraphs 1 to 21, further comprising an amino acid substitution at a position corresponding to position 105 of SEQ ID NO: 2.

Paragraph 62. The variant of paragraph 61, wherein the amino acid at substitution at a position corresponding to position 105 is substituted with Ala, Arg, Asp, Cys, Gln, Glu, Gly, His, Ile, Leu, Lys, Met, Phe, Pro, Ser, Thr, Trp, Tyr, or Val, preferably with Tyr or His.

Paragraph 63. The variant of any of paragraphs 1 to 21, further comprising an amino acid substitution at positions corresponding to positions 10, 27 and 29 of SEQ ID NO: 2.

Paragraph 64. The variant of paragraph 63, wherein the amino acid at substitution at a position corresponding to position 10 is substituted with Ala, Arg, Asn, Asp, Cys, Gln, Glu, Gly, His, Ile, Leu, Lys, Met, Phe, Pro, Ser, Thr, Trp, or Val, preferably with His; the amino acid at a position corresponding to position 27 is substituted with Ala, Arg, Asn, Asp, Cys, Gln, Glu, Gly, His, Ile, Leu, Lys, Met, Phe, Pro, Ser, Thr, Trp, or Val, preferably with Met; and the amino acid at a position corresponding to position 29 is substituted with Ala, Arg, Asp, Cys, Gln, Glu, Gly, His, Ile, Leu, Lys, Met, Phe, Pro, Ser, Thr, Trp, Tyr, or Val, preferably with Leu.

Paragraph 65. The variant of any of paragraphs 1 to 21, further comprising an amino acid substitution at positions corresponding to positions 75, 125, and 129 of SEQ ID NO: 2.

Paragraph 66. The variant of paragraph 65, wherein the amino acid at substitution at a position corresponding to position 75 is substituted with Ala, Arg, Asn, Asp, Cys, Gln, Glu, Gly, His, Ile, Leu, Lys, Met, Phe, Pro, Thr, Trp, Tyr, or Val, preferably with Ala; the amino acid at a position corresponding to position 125 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala; and the amino acid at a position corresponding to position 129 is substituted with Ala, Arg, Asn, Asp, Cys, Gln, Glu, Gly, His, Leu, Lys, Met, Phe, Pro, Ser, Thr, Trp, Tyr, or Val, preferably with Glu.

Paragraph 67. The variant of any of paragraphs 1 to 21, further comprising an amino acid substitution at positions corresponding to positions 11, 40, and 58 of SEQ ID NO: 2.

Paragraph 68. The variant of paragraph 67, wherein the amino acid at substitution at a position corresponding to position 11 is substituted with Ala, Arg, Asp, Cys, Gln, Glu, Gly, His, Ile, Leu, Lys, Met, Phe, Pro, Ser, Thr, Trp, Tyr, or Val, preferably with Asp; the amino acid at a position corresponding to position 40 is substituted with Ala, Arg, Asn, Asp, Cys, Gln, Glu, Gly, His, Ile, Leu, Lys, Met, Phe, Pro, Thr, Trp, Tyr, or Val, preferably with Arg; and the amino acid at a position corresponding to position 58 is substituted with Ala, Arg, Asn, Asp, Cys, Gln, Glu, Gly, His, Ile, Leu, Met, Phe, Pro, Ser, Thr, Trp, Tyr, or Val, preferably with Arg.

Paragraph 69. The variant of any of paragraphs 1 to 21, further comprising an amino acid substitution at one or both positions corresponding to positions 99 and 118 of SEQ ID NO: 2.

Paragraph 70. The variant of paragraph 69, wherein the amino acid at substitution at one or both positions corresponding to position 99 and 118 is substituted with Cys.

Paragraph 71. The variant of any of paragraphs 1 to 21, further comprising an amino acid substitution at a position corresponding to position 131 of SEQ ID NO: 2.

Paragraph 72. The variant of paragraph 71, wherein the amino acid at a position corresponding to position 131 is substituted with Asn.

Paragraph 73. The variant of any of paragraphs 1 to 21, further comprising an amino acid substitution at a position corresponding to position 162 of SEQ ID NO: 2 or SEQ ID NO: 4.

Paragraph 74. The variant of paragraph 73, wherein the amino acid at a position corresponding to position 73 is substituted with His.

Paragraph 75. The variant of any of paragraphs 47 to 58, which further comprises amino acid substitutions N10H, Y27M, and N29L.

Paragraph 76. The variant of paragraph 75, which further comprises amino acid substitutions S75A, Q125A and I129E.

Paragraph 77. The variant of paragraph 76, which further comprises amino acid substitutions N11D, S40R, and K58R.

Paragraph 78. The variant of paragraph 77, which further comprises amino acid substitutions S99C and Y118C.

Paragraph 79. The variant of paragraph 78, which further comprises amino acid substitution T131N.

Paragraph 80. The variant of paragraph 79, which further comprises amino acid substitution Q162H.

Paragraph 81. The variant of any of paragraphs 1-80, which has an improved thermal activity relative to a parental GH Family11 xylanase from which the variant is derived.

Paragraph 82. The variant of any of paragraphs 1-80, which has an improved thermostability relative to a parental GH Family11 xylanase from which the variant is derived.

Paragraph 83. The variant of any of paragraphs 1-80, which has an improved thermal activity and thermostability relative to a parental GH Family11 xylanase from which the variant is derived.

Paragraph 84. The variant of any of paragraphs 1-80, for which has a lower pH activity profile relative to a parental GH Family11 xylanase from which the variant is derived.

Paragraph 85. A polynucleotide encoding the variant of any of paragraphs 1-84.

Paragraph 86. A nucleic acid construct comprising the polynucleotide of paragraph 85.

Paragraph 87. An expression vector comprising the polynucleotide of paragraph 86.

Paragraph 88. A host cell comprising the polynucleotide of paragraph 85.

Paragraph 89. A method of producing a GH Family 11 xylanase variant, comprising:
a. cultivating the host cell of paragraph 88 under conditions suitable for expression of the variant; and
b. recovering the variant.

Paragraph 90. A transgenic plant, plant part or plant cell transformed with the polynucleotide of paragraph 85.

Paragraph 91. A method for obtaining a GH Family 11 xylanase variant, comprising introducing into a parent GH Family 11 xylanase an amino acid substitution at one or more positions corresponding to positions 120, 17, 24, 46, 49, 29, and 180 of the polypeptide of SEQ ID NO: 2 or SEQ ID NO: 4, wherein the variant has xylanase activity; and recovering the variant.

Paragraph 92. A composition comprising the variant of any of paragraph 1-84.

Paragraph 93. The composition of paragraph 92, further comprising one or more enzyme activities such as cellobiohydrolase, endoglucanase, beta-glucosidase, endo-beta-1,3 (4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

Paragraph 94. The composition of paragraph 92 or 93, wherein the composition is in the form of a liquid or a dry composition.

Paragraph 95. The composition of any of paragraphs 92 to 94, wherein the composition is a fermentation broth formulation or a cell composition.

Paragraph 96. The composition of any of paragraphs 92 to 95 further comprising a preservative and/or anti-microbial (e.g., bacteriostatic) agent.

Paragraph 97. A method of degrading a xylan-containing material by treating the material with a variant of any of paragraphs 1-84.

Paragraph 98. A method of degrading a xylan-containing material by treating the material with a composition of any of paragraphs 92-96.

Paragraph 99. A method for treating a pulp, comprising contacting the pulp with a variant of any of paragraphs 1-84.

Paragraph 100. A method for treating a pulp, comprising contacting the pulp with a composition of any of paragraphs 92-96.

Paragraph 101. The method of paragraph 99 or 100, wherein the treating of the pulp with the variant increases the brightness of the pulp at least 1.05-fold, e.g., at least 1.1-fold, at least 1.2-fold, at least 1.3-fold, at least 1.4-fold, at least 1.5-fold, at least 2-fold, at least 3-fold, at least 4-fold, at least 5-fold, or at least 10-fold compared to treatment with the parent.

Paragraph 102. A method for producing xylose, comprising contacting a xylan-containing material with a variant of any of paragraphs 1-84.

Paragraph 103. A method for producing xylose, comprising contacting a xylan-containing material with a composition of any of paragraphs 92-96.

Paragraph 104. A variant of GH Family 11 xylanase, comprising a substitution at one or more (e.g., several) positions corresponding to positions 120, 17, 24, 46, 49, 69, and 180 of the polypeptide of SEQ ID NO: 2 or SEQ ID NO: 4, wherein the variant has xylanase activity and wherein the variant has sequence identity of at least 60%, e.g., at least 65%, at least 70%, at least 75%, at least 80%, at least 85%, at least 90%, at least 91%, at least 92%, at least %, at least 94%, at least 95%, at least 96%, at least 97%, at least 98%, or at least 99%, but less than 100%, to amino acids 28-231 of SEQ ID NO: 8.

Paragraph 105. A variant of GH Family 11 xylanase, comprising a substitution at one or more (e.g., several) positions corresponding to positions 49, 55, 79, 82, 105, 155, and 215 of the polypeptide of SEQ ID NO: 8, wherein the variant has xylanase activity and wherein the variant has sequence identity of at least 60%, e.g., at least 65%, at least 70%, at least 75%, at least 80%, at least 85%, at least 90%, at least 91%, at least 92%, at least %, at least 94%, at least 95%, at least 96%, at least 97%, at least 98%, or at least 99%, but less than 100%, to amino acids 28-231 of SEQ ID NO: 8.

Paragraph 106. The variant of paragraph 105, wherein the amino acid at a position corresponding to position 49 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe.

Paragraph 107. The variant of any of paragraphs 105 to 106, wherein the amino acid at a position corresponding to position 55 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys.

Paragraph 108. The variant of any of paragraphs 105 to 107, wherein the amino acid at a position corresponding to position 79 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile.

Paragraph 109. The variant of any of paragraphs 105 to 108, wherein the amino acid at a position corresponding to position 82 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met or Glu.

Paragraph 110. The variant of any of paragraphs 105 to 109, wherein the amino acid at a position corresponding to position 105 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp.

Paragraph 111. The variant of any of paragraphs 105 to 110, wherein the amino acid at a position corresponding to position 155 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser.

Paragraph 112. The variant of any of paragraphs 105 to 111, wherein the amino acid at a position corresponding to position 215 of SEQ ID NO: 8 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr.

In a further embodiment the invention is characterized by the set of items herein below.

1. A GH Family 11 xylanase variant, comprising an amino acid substitution at one or more positions corresponding to positions 120, 17, 24, 46, 49, 69, and 180 of SEQ ID NO: 2 or SEQ ID NO: 4, wherein the variant has xylanase activity, and wherein the variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 2 or SEQ ID NO: 4 or amino acids 28-231 of SEQ ID NO: 8.

2. The variant item 1, which is a variant of a parent GH Family 11 xylanase selected from the group consisting of:
   a. a polypeptide having at least 60% sequence identity to SEQ ID NO: 2 or SEQ ID NO: 4;
   b. a polypeptide encoded by a polynucleotide that hybridizes under at least medium stringency conditions with (i) the mature polypeptide coding sequence of SEQ ID NO: 1, (ii) the cDNA sequence thereof, or (iii) the full-length complement of (i) or (ii);
   c. a polypeptide encoded by a polynucleotide having at least 60% identity to the mature polypeptide coding sequence of SEQ ID NO: 1 or the cDNA sequence thereof; and
   d. a fragment of SEQ ID NO: 2 or SEQ ID NO: 4, which has xylanase activity.

3. The variant of item 2, wherein the parent GH Family 11 xylanase has at least 60%, e.g., at least 65%, at least 70%, at least 75%, at least 80%, at least 85%, at least 90%, at least 97%, at least 98%, at least 99% or 100% sequence identity to SEQ ID NO: 2 or SEQ ID NO: 4.

4. The variant of item 2 or 3, wherein the parent GH Family 11 xylanase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1 or (ii) the full-length complement of (i).

5. The variant of any of items 2-4, wherein the parent GH Family 11 xylanase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 1: or the cDNA sequence thereof.

6. The variant of any of items 2-5, wherein the parent GH Family 11 xylanase comprises or consists of SEQ ID NO: 2.

7. The variant of any of items 2-5, wherein the parent GH Family 11 xylanase comprises or consists of SEQ ID NO: 4.

8. The variant of any of items 2-7, wherein the parent GH Family 11 xylanase is a fragment of SEQ ID NO: 2 or SEQ ID NO: 4, wherein the fragment has xylanase activity.

9. The variant of any of items 2-8, which has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent GH Family 11 xylanase 10. The variant of any of items 1-9, wherein the variant consists of 170 to 190, e.g., 180 to 190, or 185 to 190, amino acids.

11. The variant of any of items 1-10, wherein the number of amino acid substitutions is 1-20, e.g., 1-10 and 1-5, such as 1, 2, 3, 4, 5, 6, 7, 8, 9, 10, 11, 12, 13, 14, 15, 16, 17, 18, 19, or 20, amino acid substitutions.

12. The variant of any of items 1-11, which comprises an alteration at a position corresponding to position 120.

13. The variant of item 12, wherein the alteration is a substitution with Ser.

14. The variant of any of items 1-13, which comprises an alteration at a position corresponding to position 17.

15. The variant of item 14, wherein the alteration is a substitution with Phe.

16. The variant of any of items 1-15, which comprises an alteration at a position corresponding to position 24.

17. The variant of item 16, wherein the alteration is a substitution with Cys.

18. The variant of any of items 1-17, which comprises an alteration at a position corresponding to position 46.

19. The variant of item 18, wherein the alteration is a substitution with Ile.

20. The variant of any of items 1-19, which comprises an alteration at a position corresponding to position 49.

21. The variant of item 20, wherein the alteration is a substitution with Met or Glu.

22. The variant of any of items 1-21, which comprises an alteration at a position corresponding to position 69.

23. The variant of item 22, wherein the alteration is a substitution with Asp.

24. The variant of any of items 1-23, which comprises an alteration at a position corresponding to position 180.

25. The variant of item 24, wherein the alteration is a substitution with Tyr.

26. The variant of any of items 1-25, which comprises an alteration at two positions corresponding to any of positions 120, 17, 24, 46, 49, 69, and 180.

27. The variant of any of items 1-25, which comprises an alteration at three positions corresponding to any of positions 120, 17, 24, 46, 49, 69, and 180.

28. The variant of any of items 1-25, which comprises an alteration at four positions corresponding to any of positions 120, 17, 24, 46, 49, 69, and 180.

29. The variant of any of items 1-25, which comprises an alteration at five positions corresponding to any of positions 120, 17, 24, 46, 49, 69, and 180.

30. The variant of any of items 1-25, which comprises an alteration at six positions corresponding to any of positions 120, 17, 24, 46, 49, 69, and 180.

31. The variant of any of items 1-25, which comprises an alteration at each position corresponding to any of positions 120, 17, 24, 46, 49, 69, and 180.

32. The variant of any of items 1-31, which comprises one or more substitutions selected from the group consisting of T120S, Y17F, G24C, V46I, K49M, K49E, N69D, and F180Y.

33. The variant of item 32, which comprises T120S.

34. The variant of item 32, which further comprises one or more of N10Q, L105H, L105Y or Q162H.

35. The variant of item 34, which comprises T120S and L105Y.

36. The variant of item 34, comprises T120S, L105Y, Q162H, and F180Y.

37. The variant of item 34 which comprises T120S, N10Q, K49E, H105Y, Q162H, and F180Y.

38. The variant of item 34, which comprises T120S, G24C, L105Y, Q162H, and F180Y.
39. The variant of any of items 1-38, which has an improved thermal activity, thermostability, or both, relative to a parental GH11 xylanase from which the variant is derived.
40. The variant of any of items 1-38, which has a lower pH activity profile relative to a parental GH11 xylanase from which the variant is derived.
41. A polynucleotide encoding the variant of any of items 1-40.
42. A nucleic acid construct comprising the polynucleotide of item 41.
43. An expression vector comprising the polynucleotide of item 41.
44. A host cell comprising the polynucleotide of item 41.
45. A method of producing a GH Family 11 xylanase variant, comprising:
    a. cultivating the host cell of item 44 under conditions suitable for expression of the variant; and
    b. recovering the variant.
46. A transgenic plant, plant part or plant cell transformed with the polynucleotide of item 41.
47. A method of producing a variant of any of items 1-40, comprising:
    a. cultivating a transgenic plant or a plant cell comprising a polynucleotide encoding the variant under conditions conducive for production of the variant; and
    b. recovering the variant.
48. A method for obtaining a GH Family 11 xylanase variant, comprising introducing into a parent GH Family 11 xylanase an amino acid substitution at one or more positions corresponding to positions 120, 17, 24, 46, 49, 69 and 180 of the polypeptide of SEQ ID NO: 2 or SEQ ID NO: 4, wherein the variant has xylanase activity; and recovering the variant.
49. A composition comprising the variant of any of paragraph 1-40.
50. The composition of item 49, further comprising one or more enzyme activities selected from the group consisting of: cellobiohydrolase, endoglucanase, beta-glucosidase, endo-beta-1,3(4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.
51. The composition of item 49 or 50, wherein the composition is in the form of a liquid or a dry composition.
52. The composition of any of items 49-51, wherein the composition is a fermentation broth formulation or a cell composition.
53. The composition of any of items 49-52, further comprising a preservative and/or anti-microbial (e.g., bacteriostatic) agent.
54. A method of degrading a xylan-containing material by treating the material with a variant of any of items 1-40.
55. A method of degrading a xylan-containing material by treating the material with a composition of any of items 49-52.
56. A method for treating a pulp, comprising contacting the pulp with a variant of any of items 1-40.
57. A method for treating a pulp, comprising contacting the pulp with a composition of any of items 49-52.
58. A method for producing xylose, comprising contacting a xylan-containing material with a variant of any of items 1-40.
59. A method for producing xylose, comprising contacting a xylan-containing material with a composition of any of items 49-52.

---

What is claimed is:

1. A GH Family 11 xylanase variant, comprising an amino acid substitution at three or more positions corresponding to positions 120, 17, 24, 46, 49, 69, and 180 of SEQ ID NO: 2 or SEQ ID NO: 4, wherein the variant has xylanase activity, and wherein the variant has at least 90%, but less than 100% sequence identity to SEQ ID NO: 2 or SEQ ID NO: 4 or amino acids 28-231 of SEQ ID NO: 8.

2. The variant claim 1, which is a variant of a parent GH Family 11 xylanase selected from the group consisting of:
   a. a polypeptide having at least 90% sequence identity to SEQ ID NO: 2 or SEQ ID NO: 4;
   b. a polypeptide encoded by a polynucleotide that hybridizes under at least medium stringency conditions with (i) the mature polypeptide coding sequence of SEQ ID NO: 1, (ii) the cDNA sequence thereof, or (iii) the full-length complement of (i) or (ii);
   c. a polypeptide encoded by a polynucleotide having at least 90% identity to the mature polypeptide coding sequence of SEQ ID NO: 1 or the cDNA sequence thereof; and
   d. a fragment of SEQ ID NO: 2 or SEQ ID NO: 4, which has xylanase activity.

3. The variant of claim 1, wherein the variant consists of 170 to 190 amino acids.

4. The variant of claim 1, wherein the number of amino acid substitutions is 3-7 amino acid substitutions.

5. The variant of claim 1, which comprises an alteration at four positions corresponding to any of positions 120, 17, 24, 46, 49, 69, and 180.

6. The variant of claim 1, which comprises an alteration at each position corresponding to positions 120, 17, 24, 46, 49, 69, and 180.

7. The variant of claim 1, which comprises three or more substitutions selected from the group consisting of T120S, Y17F, G24C, V46I, K49M, K49E, N69D, and F180Y.

8. The variant of claim 1, which has an improved thermal activity, thermostability, or both, relative to a parental GH11 xylanase having the same amino acid sequence as the variant except for substitution at the three or more positions correspond to positions 120, 17, 24, 46, 49, 69 and 180.

9. The variant of claim 1, which has a lower pH activity profile relative to a parental GH11 xylanase having the same amino acid sequence as the variant except for substitution at the three or more positions correspond to positions 120, 17, 24, 46, 49, 69 and 180.

10. A polynucleotide encoding the variant of claim 1.

11. A nucleic acid construct comprising the polynucleotide of claim 10.

12. An expression vector comprising the polynucleotide of claim 10.

13. A host cell comprising the polynucleotide of claim 10.

14. A method of producing a GH Family 11 xylanase variant, comprising:
   a. cultivating the host cell of claim 13 under conditions suitable for expression of the variant; and
   b. recovering the variant.

15. A method of degrading a xylan-containing material by treating the material with a variant of claim 1.

* * * * *

SEQUENCE LISTING

```
<160> NUMBER OF SEQ ID NOS: 8

<210> SEQ ID NO 1
<211> LENGTH: 780
<212> TYPE: DNA
<213> ORGANISM: Trichoderma reesei

<400> SEQUENCE: 1
atggtctcct tcacctccct cctcgccggc gtcgccgcca tctcgggcgt cttggccgct      60
cccgccgccg aggtcgaatc cgtggctgtg gagaagcgcc agacgattca gcccggcacg     120
ggctacaaca acggctactt ctactcgtac tggaacgatg ccacggcgg cgtgacgtac      180 accaatggtc ccggcgggca gttctccgtc aactggtcca actcgggcaa ctttgtcggc     240
ggcaagggat ggcagcccgg gaccaagaac aagtaagact acctactctt acccccttttg    300 accaacacag cacaacacaa tacaacacat gtgactacca atcatggaat cggatctaac     360
agctgtgttt taaaaaaaag ggtcatcaac ttctcgggaa gctacaaccc caacggcaac     420
agctacctct ccgtgtacgg ctggtccgc aaccccctga tcgagtacta catcgtcgag      480
aactttggca cctacaaccc gtccacgggc gccaccaagc tgggcgaggt cacctccgac     540
ggcagcgtct acgacattta ccgcacgcag cgcgtcaacc agccgtccat catcggcacc     600
```

```
gccaccttttt accagtactg gtccgtccgc cgcaaccacc gctcgagcgg ctccgtcaac    660
acggcgaacc acttcaacgc gtgggctcag caaggcctga cgctcgggac gatggattac    720
cagattgttg ccgtggaggg ttactttagc tctggctctg cttccatcac cgtcagctaa    780
```

<210> SEQ ID NO 2
<211> LENGTH: 190
<212> TYPE: PRT
<213> ORGANISM: Trichoderma reesei

<400> SEQUENCE: 2

```
Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 3
<211> LENGTH: 223
<212> TYPE: PRT
<213> ORGANISM: Trichoderma reesei

<400> SEQUENCE: 3

```
Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Gln Thr Ile Gln Pro Gly Thr Gly Tyr Asn Asn Gly Tyr Phe Tyr
        35                  40                  45

Ser Tyr Trp Asn Asp Gly His Gly Gly Val Thr Tyr Thr Asn Gly Pro
    50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110
```

Ser Arg Asn Pro Leu Ile Glu Tyr Tyr Ile Val Glu Asn Phe Gly Thr
        115                 120                 125

Tyr Asn Pro Ser Thr Gly Ala Thr Lys Leu Gly Glu Val Thr Ser Asp
        130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
        210                 215                 220

<210> SEQ ID NO 4
<211> LENGTH: 190
<212> TYPE: PRT
<213> ORGANISM: Artificial sequence
<220> FEATURE:
<223> OTHER INFORMATION: Synthetic construct

<400> SEQUENCE: 4

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
            20                  25                  30

Gly Gln Phe Ser Val Asn Trp Arg Asn Ser Gly Asn Phe Val Gly Gly
        35                  40                  45

Lys Gly Trp Gln Pro Gly Thr Lys Asn Arg Val Ile Asn Phe Ser Gly
50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Cys Thr Gly Ala Thr Lys His Gly Glu Val Thr Ser Asp Gly
            100                 105                 110

Ser Val Tyr Asp Ile Cys Arg Thr Gln Arg Val Asn Ala Pro Ser Ile
        115                 120                 125

Glu Gly Asn Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 5
<211> LENGTH: 17
<212> TYPE: DNA
<213> ORGANISM: Artificial sequence
<220> FEATURE:
<223> OTHER INFORMATION: Synthetic construct

<400> SEQUENCE: 5
tggctgtgga gaagcgc                                                  17

<210> SEQ ID NO 6
<211> LENGTH: 23
<212> TYPE: DNA
<213> ORGANISM: Artificial sequence
<220> FEATURE:
<223> OTHER INFORMATION: Synthetic construct

<400> SEQUENCE: 6

```
gcaacacctg gcaattcctt acc                                              23
```

<210> SEQ ID NO 7
<211> LENGTH: 696
<212> TYPE: DNA
<213> ORGANISM: Dictyoglomus thermophilum

<400> SEQUENCE: 7

```
atgaagaaac cgttggggaa aattgtcgca agcaccgcac tactcatttc tgttgctttt      60
agttcatcga tcgcatcggc tgctcagaca tcaatcacac ttacatctaa cgcatcaggc     120
acattcgacg gctattacta cgagctttgg aaggacacag caacgacta tatgactgta     180
tacactcaag gtcgcttctc atgccagtgg tctaacatca caacgcgct tttccgcacg     240
ggcaagaagt acaaccagaa ctggcaatct cttggcacta tccgcatcac ttattctgcg     300
acatacaacc cgaacggcaa ctcttacctt tgtatctacg gctggtctac gaacccgctt     360
gttgagttct acatcgtaga gtcttggggc aactggcgtc ctcctggcgc aacatctctt     420
ggccaggtta caatcgatgg tgcacatat gacatctacc gcactactcg cgttaaccag     480
cctagcatcg ttggcacagc tactttcgac caatactgga gcgttcgcac tagcaagcgc     540
acatctggca cagttacggt tacgaccac tttcgcgcat gggcaaatcg tggccttaac     600
cttggcacaa tcgaccaaat cacactttgt gttgagggc accagtcttc tggcagcgca     660
aacatcactc aaaacacttt ctctcagggc agctaa                              696
```

<210> SEQ ID NO 8
<211> LENGTH: 231
<212> TYPE: PRT
<213> ORGANISM: Dictyoglomus thermophilum

<400> SEQUENCE: 8

```
Met Lys Lys Pro Leu Gly Lys Ile Val Ala Ser Thr Ala Leu Leu Ile
1               5                   10                  15

Ser Val Ala Phe Ser Ser Ile Ala Ser Ala Ala Gln Thr Ser Ile
            20                  25                  30

Thr Leu Thr Ser Asn Ala Ser Gly Thr Phe Asp Gly Tyr Tyr Tyr Glu
        35                  40                  45

Leu Trp Lys Asp Thr Gly Asn Thr Thr Met Thr Val Tyr Thr Gln Gly
    50                  55                  60

Arg Phe Ser Cys Gln Trp Ser Asn Ile Asn Asn Ala Leu Phe Arg Thr
65                  70                  75                  80

Gly Lys Lys Tyr Asn Gln Asn Trp Gln Ser Leu Gly Thr Ile Arg Ile
                85                  90                  95

Thr Tyr Ser Ala Thr Tyr Asn Pro Asn Gly Asn Ser Tyr Leu Cys Ile
            100                 105                 110

Tyr Gly Trp Ser Thr Asn Pro Leu Val Glu Phe Tyr Ile Val Glu Ser
        115                 120                 125

Trp Gly Asn Trp Arg Pro Pro Gly Ala Thr Ser Leu Gly Gln Val Thr
    130                 135                 140
```

```
Ile Asp Gly Gly Thr Tyr Asp Ile Tyr Arg Thr Arg Val Asn Gln
145                 150                 155                 160

Pro Ser Ile Val Gly Thr Ala Thr Phe Asp Gln Tyr Trp Ser Val Arg
                165                 170                 175

Thr Ser Lys Arg Thr Ser Gly Thr Val Thr Val Thr Asp His Phe Arg
            180                 185                 190

Ala Trp Ala Asn Arg Gly Leu Asn Leu Gly Thr Ile Asp Gln Ile Thr
        195                 200                 205

Leu Cys Val Glu Gly Tyr Gln Ser Ser Gly Ser Ala Asn Ile Thr Gln
        210             215                 220

Asn Thr Phe Ser Gln Gly Ser
225                 230
```